(12) United States Patent
Sato et al.

(10) Patent No.: US 6,322,996 B1
(45) Date of Patent: *Nov. 27, 2001

(54) PROTEIN MODIFICATION METHOD

(75) Inventors: Haruya Sato; Keiji Yamamoto; Kokichi Suzuki, all of Chiba-ken; Masahiro Ikeda, Tokyo; Masahiro Sakagami, Chiba-ken; Makoto Taniguchi, Saitama-ken, all of (JP)

(73) Assignee: Drug Delivery System Institute, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/505,250

(22) PCT Filed: Feb. 27, 1995

(86) PCT No.: PCT/JP95/00298

§ 371 Date: Nov. 29, 1995

§ 102(e) Date: Nov. 29, 1995

(87) PCT Pub. No.: WO96/06181

PCT Pub. Date: Feb. 29, 1996

(30) Foreign Application Priority Data

Aug. 23, 1994 (JP) .................................................. 6-198187

(51) Int. Cl.⁷ ........................ C07C 211/61; C07K 1/107; C07K 1/12; C12P 13/00
(52) U.S. Cl. ........................ 435/68.1; 435/128; 530/402; 530/409; 530/411; 562/563; 564/463; 564/511
(58) Field of Search .................................. 530/402, 403, 530/405, 409, 411; 562/563, 561; 564/497, 498, 499, 511, 512, 463; 435/68.1, 128

(56) References Cited

U.S. PATENT DOCUMENTS 5,490,980 * 2/1996 Richardson et al. ............... 424/94.6

OTHER PUBLICATIONS

Usui et al J. Biological Chemistry 1993 vol. 268, No. 17 pp. 12311–12316 Propolypeptide of von Willebrand Factor Serves as a Substrate for Factor XIIIa and is Cross–Linked to Laminin.
Mariniello et al Eur. J. Biochem. 215, 99–104 FEBS 1993 "Human–immunodeficiency–virus transmembrane glycoprotein gp41 is an amino acceptor and donor substrate for transglutaminase in vitro".
Agricultural and Biological Chemistry, vol. 48, No. 9 Sep. 1984 pp. 2347–2354 Ikura et al Use of transglutaminase reversible blocking of amino groups in substrate proteins for a high yield of specific products.
Agricultural and Biological Chemistry, vol. 45, No. 11, Nov. 1981 pp. 2587–2592 Ikura et al "Incorporation of amino acids into food proteins by transglutaminase".
Derwent AN 196323 XP002027523 "Modified protein peptide residue comprise treat substrate at high pressure before adding transglutaminase" & JP 07 111 897 A May 1995.
Biochemistry, vol. 23, No. 16 Jul. 1984 pp. 3759–3765 XP002027518 "Neoglycoproteins: in vitro induction of glycosyl units at glutamines in beta–casein using transglutaminase".
Chemical Abstracts, vol. 112, No. 19, May 1990 abstract No. 174618 XXXX(002027511 &Biochem J. vol. 265, No. 3, 1990 pp. 707–713 Cocuzzi et al "Post–transational modification of apolipoprotein B by transglutaminases".
Proceedings of the National Academy of Sciences of USA, vol. 87, No. 21, Nov. 1990 pp. 8472–8475, XP0027519 Parameswan et al "Labeling of epsilon–lysine crosslinking sites in proteins with peptide substrates of factor XIIIa and transglutaminase".
Lorand et al. "Modification of Human Erythrocyte Ghosts". Biochemical and Biophysical research Communications. vol. 67, No. 3, pp. 1158–1165, 1975.*
Parameswaran et al. "labelling of E–Lysine crosslinking sites in proteins with peptide substrates of factor XIIIa and transglutaminase". PNAS. vol. 87, pp. 8472–8475, Nov. 1990.*
Cordella–Miele et al. "Transglutaminase–catalyzed Incorporation of Polyamines into Phospholipase A2". J. Biochem. vol. 113, pp. 164–173, 1993.*
Abad et al. "Peptide binding to lipid bilayers: New insight from active fluorescent peptides labelled with dansylcadaverine probe". Pept. 1994, Proc. Eur. Symp., 23rd (1995), Meeting Date 1994, pp. 773–774.*

* cited by examiner

*Primary Examiner*—Donna C. Wortman
*Assistant Examiner*—Brenda G. Brumback
(74) *Attorney, Agent, or Firm*—Oblon, Spivak, Mclleland, Maier & Neustadt, P.C.

(57) ABSTRACT

Transglutaminase is allowed to act upon both a physiologically active protein (inclusive of a fused protein thereof with a peptide through acid amide bonding) and an amino group donor containing the polyethylene glycol, polysaccharide, polyamino acid or branched type sugar derivative moiety, whereby the physiologically active protein is modified without spoiling its inherent physiological activities, and may be improved in its qualification as a drug.

10 Claims, 9 Drawing Sheets

PROTEIN MODIFICATION METHOD

TECHNICAL FIELD

This invention relates to a method of the modification of a Gln residue in the peptide moiety of a fused protein in which a peptide is linked through the amide bonding to the N-terminal or C-terminal or to the amino acid sequence of a physiologically active protein, more particularly a method of the selective modification of a Gln residue in a physiologically active protein with polyethylene glycol, a polysaccharide, a polyamino acid or a branched sugar derivative.

BACKGROUND ART

Recently, a number of physiologically active proteins are used or ready to be used as pharmaceutical drugs. Since these physiologically active proteins are all easily metabolized, decomposed or excreted when administered to the body of animals including human beings, their retention time in blood is short and their target directivity is low, thus posing a problem in that the protein is not accumulated in the affected part in a required amount for a required period of time.

Various attempts have been made with the aim of overcoming this problem. For example, as described in a report by Karte et al (*Proc. Natl. Acad. Sci., USA*, 84 (1987), pp.1487–1491), there is a method in which a physiologically active protein is chemically modified with polyethylene glycol.

However, all such chemical modification methods find difficulty in modifying a specified part of the protein or strictly controlling the degree of modification. For example, when a protein is modified with polyethylene glycol, polyethylene glycol is introduced mainly at the ε-position amino group of a lysine residue in the protein, but, since a protein molecule generally contains a plurality of lysine residues, polyethylene glycol may be incorporated or not incorporated into a plurality of lysine residues. As the result, the protein loses its inherent physiological activity in some cases or its quality as a pharmaceutical drug cannot be controlled easily.

For these reasons, great concern has been directed toward the development of a method which can modify a specified site of a physiologically active protein or can strictly control degree of the modification when the physiologically active protein is modified with a modification agent such as polyethylene glycol, a polysaccharide or the like.

DISCLOSURE OF THE INVENTION

The inventors of the present invention have found that the physiologically active protein can be modified in a position-selective manner with polyethylene glycol, a polysaccharide, a polyamino acid or a branched sugar derivative, and the modification degree can be controlled strictly, when a physiologically active protein having a molecular weight of from $5 \times 10^3$ to $2 \times 10^5$ and containing at least one glutamine residue capable of receiving the action of transglutaminase is allowed to react with an amino group donor in the presence of transglutaminase, thereby effecting the formation of amido linkage between the γ-carboxyamido group of said glutamine residue and the primary amino group of said amino group donor, and have accomplished the present invention on the basis of these findings.

Accordingly, the present invention relates to a method of modifying protein which comprises allowing a physiologically active protein having a molecular weight of from $5 \times 10^3$ to $2 \times 10^5$ and containing at least one glutamine residue to react with an amino group donor represented by any one of the following general formulae (I) to (IV) or an alkylamine-introduced polysaccharide or a modified product thereof in the presence of transglutaminase, thereby effecting the formation of amido linkage between the γ-carboxyamido group of said glutamine residue and the primary amino group of the amino group donor.

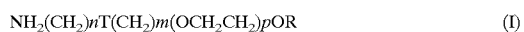

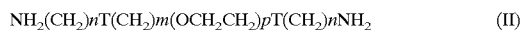

In the above general formulae (I) and (II), n is an integer of 1 to 8, m is an integer of 0 to 2, p is an integer of 1 to 400, T represents a bond selected from —O—, —C(O)O—, —OC(O)—, —NHCO—, —OCNH—, —NHCONH—, —OOCNH— or —HNCOO—, and R represents a hydrogen atom, a lower alkyl group having 1 to 5 carbon atoms or a lower acyl group having 2 to 6 carbon atoms.

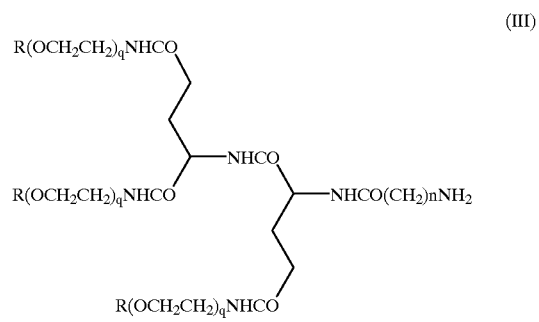

In the above general formula (III), n is an integer of 1 to 8, q is an integer of 2 to 6, and R represents a galactose, a glucose or an N-acetylgalactosamine.

In the above general formula (IV), n is an integer of 1 to 8, and T' represents the residue of a polyamino acid excluding its terminal carboxyl group. In this connection, component amino acids of the polyamino acid are not particularly limited, but an acidic or basic amino acid may be preferred from the viewpoint of solubility. Also, preferred amino acid polymerization degree is 1 to 400.

The alkylamine-introduced polysaccharide or a modified product thereof is a compound obtained by subjecting the reducing end-group of a polysaccharide to reductive amination in the presence of a compound represented by the following general formula (1) or a salt thereof (hydrochloride or the like) and then eliminating the protecting group V.

In the above general formula (1), n is an integer of 1 to 8, and V represents a protecting group generally used for the protection of an amino group such as Fmoc (9H-fluoren-9-ylmethoxycarbonyl).

Examples of such polysaccharide include pullulan, dextran, dextran sulfate, chondroitin sulfate and carboxymethylated products thereof, having a molecular weight of $1 \times 10^3$ to $1 \times 10^5$ dalton.

The alkylamine-introduced polysaccharide or a modified product thereof can be obtained for example by dissolving a polysaccharide or a carboxymethylated polysaccharide in an acetic acid-water-DMF mixture solution or in water, successively adding to the resultant solution a compound of the above general formula (1) in an amount of about 10 to 1000 equivalents, more preferably about 100 equivalents, per 1 equivalent of the polysaccharide and a reducing agent such as sodium cyanoboron hydride, maintaining the mixture at a temperature of from room temperature to 80° C., more preferably from 50 to 70° C., for 1 to 3 days whereby the reaction is carried out, and then eliminating the amino group-protecting group with an alkali such as diethylamine or 0.1 N NaOH.

The aforementioned physiologically active protein has a molecular weight of $5 \times 10^3$ or more, and dansyl cadaverine can be introduced thereinto when 10 $\mu$M of said physiologically active protein and monodansylcadaverine in an amount of 100 equivalents per 1 equivalent of said physiologically active protein are kept at 37° C. for 60 minutes in a 100 mM Tris-HCl buffer solution containing 10 mM $CaCl_2$ and having a pH value of 7.5, in the presence of the aforementioned transglutaminase.

The present invention will be described in detail, as follows.

Examples of the physiologically active protein to be modified with polyethylene glycol, a polysaccharide, a polyamino acid or a branched sugar derivative by the method of the present invention include human blood plasma components such as albumin, immunoglobulin, blood coagulation factors and the like; enzymes such as superoxide dismutase, urokinase and the like; hormones such as growth hormone, erythropoietin and the like; cell growth regulating factors such as cell growth factors, cell growth inhibitors and the like; immune reaction controlling factors such as cell differentiation, induction, stimulation and the like factors; and biologically active cellular proteins such as monokine, cytokine, lymphokine and the like. Origins of these physiologically active proteins are not particularly limited, which include animals, plants and microorganisms. Also useful are proteins which are produced by integrating genes of the above proteins into *Escherichia coli,* yeast, Chinese hamster ovary and the like and expressing the integrated genes.

Physiologically active proteins if having a molecular weight of smaller than $5 \times 10^3$ have a smaller number of lysine residues and the like, and can be controlled to a certain degree with respect to modification quantity, modified position and the like even though by a chemical modification method. The effects of the present invention can therefore be exhibited more efficiently with respect to physiologically active proteins having a molecular weight of $5 \times 10^3$ or more. The physiologically active protein of the present invention should contain at least one, preferably one or two, glutamine residues capable of receiving the action of transglutaminase. Whether the glutamine residue(s) in the protein molecule can receive the action of transglutaminase is examined in the following manner. A 10 $\mu$M portion of a physiologically active protein and monodansylcadaverine in a 100 equivalent amount per 1 equivalent of the physiologically active protein are kept at 37° C. for 60 minutes in a 100 mM Tris-HCl buffer containing 10 mM $CaCl_2$ and having a pH value of 7.5 in the presence of transglutaminase. Whether the monodansylcadaverine has been introduced or not can be confirmed by whether the protein-originated peak resultant from the reverse phase HPLC analysis gives a fluorescence absorption.

The transglutaminase to be used in the process of the present invention can be obtained from various origins with no particular limitation, such as from various animal tissues, blood plasma components, and microorganisms.

Transglutaminase, an enzyme which catalyzes the acyl transfer reaction between the γ-carboxyamido group of a glutamine (Gln) residue in protein or a peptide chain and the ε-amino group of a lysine (Lys) residue or various alkylamines, is widely found in various animal tissues, blood cells, blood plasma and the like, in various molecular forms. This enzyme catalyzes the cross-linking reaction through the ε-(γ-glutamyl) lysine-isopeptide bond, and cross-linking fibrin molecules at the last step in blood coagulation, as well as it is found to be concerned with keratinization of epidermis cells, coagulation of seminal fluid, healing of wounded tissues, and the like. Since transglutaminase has a very high substrate specificity to the Gln residue, there is a possibility that only certain Gln residues in the protein may be modified with an alkylamine. E.g., an alkylamine having a terminal sugar unit was introduced into β-casein at its certain Gln residue(s), with the use of transglutaminase (TGase) originating from guinea pig liver (Yan, S. C. B. et al, (1984) Biochemistry, 23, 3759–3765). Furthermore, a lower molecular weight spermine derivative was introduced into apolipoprotein B at its Gln residue(s), with the use of blood coagulation factor XIII (Factor XIII), a transglutaminase found in blood plasma (Cocuzzi, E. et al, (1990), Biochem. J., 265, 707–713). As explained just above, the application of transglutaminase has hitherto been restricted only to the introduction of a lower molecular weight alkylamine into a protein already having Gln residue(s) as the substrate, and has never been made for the introduction of a high molecular weight synthetic compound such as PEG or the like.

When a protein has no glutamine residues capable of receiving the action of transglutaminase, glutamine residue(s) can be introduced into the protein by preparing a fused protein composed of the protein and a peptide which contains one or two, preferably one, glutamine residue capable of receiving the action of transglutaminase. In this case, such a starting protein has a molecular weight of from $5 \times 10^3$ to $2 \times 10^5$. Also, it should have a physiological activity.

In order to suppress side reactions to the minimum, it is desirable to purify the physiologically active protein.

The aforementioned peptide is composed of 3 to 20 α-L-amino acid residues and has a glutamine residue between at or after the second position from its N-terminal and at or before the second position from its C-terminal, into which peptide monodansylcadaverine can be introduced when 10 $\mu$M of said peptide and monodansylcadaverine in a 100 equivalent amount per 1 equivalent of said peptide are kept at 37° C. for 60 minutes in a 100 mM Tris-HCl buffer containing 10 mM $CaCl_2$ and having a pH value of 7.5 in the presence of the aforementioned transglutaminase.

According to the findings by the present inventors, those peptides into which monodansylcadaverine can be introduced under such conditions can react with an amino group donor represented by any one of the aforementioned general formulae (I) to (IV) or an alkylamine-introduced polysaccharide or a modified product thereof by the action of transglutaminase, while those peptides into which monodansylcadaverine can not be introduced under such conditions do not react with these amino group donors by the same enzyme.

Though the peptide should be composed of at least 3 amino acid residues, too many residues will exert influence upon the properties of the protein and require complex steps for its synthesis.

Illustrative examples of the peptide are shown in Table 1.

TABLE 1

| | | | | |
|---|---|---|---|---|
| QAQSKGNPE | Q | TPVLKPEEEA | (SEQ ID NO: 1) | |
| RGTCVAAED | Q | RPINYCETGL | (SEQ ID NO: 2) | |
| VDGGCSHLG | Q | SYADRDVWKP | (SEQ ID NO: 3) | |
| SSGTGSTGN | Q | NPGSPRPGST | (SEQ ID NO: 4) | |
| ESSVSGSTG | Q | WHSESGSFRP | (SEQ ID NO: 5) | |
| NRLTIGEGQ | Q | HHLGGAKQAG | (SEQ ID NO: 6) | |
| EA | Q | QIVQPQSPLT | (SEQ ID NO: 7) | |
| KPKMCPQLQ | Q | YEMHGPEGLR | (SEQ ID NO: 8) | |
| N | Q | EQ | (SEQ ID NO: 9) | |
| HS | Q | GTFTSDYSKY | (SEQ ID NO: 10) | |
| SKYLDSRRA | Q | DFVQWLMNT | (SEQ ID NO: 11) | |
| PPQSVLSLS | Q | SKVLPVPEKA | (SEQ ID NO: 12) | |
| ALW | Q | FRSMIKCAIP | (SEQ ID NO: 13) | |
| AKKKRSRFD | Q | DVLN | (SEQ ID NO: 14) | |
| LISWIKRKR | Q | Q | (SEQ ID NO: 15) | |
| QAWFIENEE | Q | EYVQTVKSSK | (SEQ ID NO: 16) | |
| PSIVGRPRH | Q | GVMVGMGQKD | (SEQ ID NO: 17) | |
| ASNHET | Q | AGKPQPLNPK | (SEQ ID NO: 18) | |
| AE | Q | HSTPEQAAAG | (SEQ ID NO: 19) | |
| ETQTV | Q | QELESLPTTK | (SEQ ID NO: 20) | |
| EAQLELPEQ | Q | VGQPKHLEQQ | (SEQ ID NO: 21) | |
| SSGGGGFSG | Q | AVQCQSYGGV | (SEQ ID NO: 22) | |
| GSGSGYVSS | Q | QVTQTSCAPQ | (SEQ ID NO: 23) | |
| GYVSSQQVT | Q | TSCAPQPSYG | (SEQ ID NO: 24) | |
| KYGVTDKIS | Q | VSTGGGASLE | (SEQ ID NO: 25) | |
| GGFMYSDKS | Q | TPLV | (SEQ ID NO: 26) | |
| MRPKP | Q | QFFGLM | (SEQ ID NO: 27) | |
| RFSNCGLGS | Q | AGIRDMRGGF | (SEQ ID NO: 28) | |

Meaning of the single letter code in Table 1 is shown in Table 2.

TABLE 2

| | |
|---|---|
| G | glycine |
| A | alanine |
| V | valine |
| L | leucine |
| I | isoleucine |
| S | serine |
| T | threonine |
| C | cysteine |
| M | methionine |
| D | aspartic acid |
| E | glutamic acid |
| N | asparagine |
| Q | glutamine |
| K | lysine |
| H | histidine |
| R | arginine |
| F | phenylalanine |
| Y | tyrosine |
| W | tryptophan |
| P | proline |

In the above-mentioned peptides, the glutamine residues shown as a 10th residue counted from the N-terminal serve as the substrate by transglutaminase. The peptides described above can be used, even when amino acid residue(s) have been removed from the N-terminal or C-terminal thereof. The peptides composed of less than 20 residues can be also used, even when amino acid residue(s) have been added thereto. In addition, some amino acid residue(s) in the above peptides may be substituted with other amino acid residue (s), with the proviso that reactivity of the glutamine residue as the substrate by transglutaminase does not change greatly.

A fused protein composed of the aforementioned protein and the aforementioned peptide can be prepared by introducing the peptide at the N-terminal or C-terminal of the protein or at the amino acid sequence of the protein. Introduction of the peptide into the protein may be effected simply and easily by preparing a corresponding DNA fragment and expressing the DNA fragment in a microbial host.

Illustratively, such fused proteins may be prepared in the following manner.

The introduction at the N-terminal may be carried out, e.g., as described in Examples 1 to 6. A human interleukin-2 (hIL-2) expression plasmid pT13SNCo (N. Tonouchi et al., *J. Biochem.*, 104, 30–34 (1988)) is digested with restriction enzymes ClaI and NcoI and ligated with a synthetic DNA fragment derived from a peptide shown in Table 1. The thus constructed plasmid is transformed into an *E. coli* strain to allow the strain to produce a fused protein in which the peptide containing a Gln residue is introduced at the N-terminal.

The introduction at the C-terminal can be effected, e.g., in accordance with the human superoxide dismutase (SOD)-related fused protein construction method (M. Inoue et al., *FEBS LETTERS* (1990) 269, 1, 89–92). That is, an SOD expression plasmid PBRSOD is digested with restriction enzymes BamHI and SalI and ligated with a synthetic DNA fragment derived from a peptide shown in Table 1, such as Met-Lys-Pro-Gln-Gln-Phe-Phe-Gly-Leu (SEQ ID NO:29). The thus constructed plasmid is transformed into a yeast strain to allow the strain to produce a fused protein in which the peptide containing a Gln residue is introduced at the C-terminal of SOD.

The introduction at the amino acid sequence can be carried out, e.g., as follows. An expression plasmid is constructed in which a DNA sequence of the hIL-2 expression plasmid is partly substituted so that the N-terminal side 5 amino acid residues of hIL-2 are changed from Ala-Pro-Tyr-Ser-Ser (SEQ ID NO:30) to Lys-Pro-Gln-Gln-Phe (SEQ ID NO:31). The thus constructed plasmid is transformed into an *E. coli* strain to allow the strain to produce a fused protein in which a Gln residue-containing peptide is introduced into the amino acid sequence, replacing the N-terminal side 5 amino acid residues of hIL-2.

The vector to be used for the introduction of a desired DNA is not particularly limited, and any vector so far known may be used. For example, the following vectors may be used. That is, vectors (stringent type: pSC101, pRK353, pRK646, pRK248, pDF41 and the like, and EK type plasmid vectors (relaxed type: ColE1, pVH51, pAC105, RSF2124, pCR1, pMB9, pBR313, pBR322, pBR324, pBR325, pBR327, pBR328, pKY2289, pKY2700, pKN80, pKC7, pKB158, pMK2004, pACYC1, pACYC184, dul and the like) and λgt type phage vectors (λ.gt.λc, λ.gt.λB, $\lambda_{WES}$.λC, $\lambda_{WES}$.λB, $\lambda_{ZJ}$vir., λB, $\lambda_{ALO}.\lambda_B$, $\lambda_{WES}$.Ts$_{622}$, $\lambda_D$am and the like).

Hosts for these vectors are also not particuarly limited, and bacteria, yeasts and the like may be used, out of which *E. coli* is well studied and therefore particularly useful.

The amino group donors, being polyethylene glycol derivatives, are compounds represented by the aforementioned general formula (I) or (II). No special methods are required for the preparation of these amino group donors, as will be described in the following.

Firstly, synthesis of the compounds of the general formula (I) can be effected, in the following manner for example.

That is, in the case the bonding T is an acid amide bonding, the compound of interest can be obtained by a method in which an alkylamine having an amino group (Ta) and a methoxypolyethylene glycol having a carboxylic group (Tb), or the two compounds having the reverse relation in respect of Ta and Tb, are allowed to react with each other under dehydration condensation conditions, namely, in an inert solvent (for example, acetonitrile, dimethylformamide, methylene chloride, ethylene chloride or the like) in the presence of an appropriate catalyst (for example, N-hydroxysuccinimide, N,N'-dicyclohexylcarbodiimide, 1-hydroxybenzotriazole or the like), at a reaction temperature of from 0° C. to room temperature for 1 to 24 hours.

Also, in the case the bonding T is an ester bonding, the compound of interest can be obtained by a method in which an alkylamine having a hydroxyl group (Ta) and a methoxypolyethylene glycol having a carboxylic group (Tb), or the two compounds having the reverse relation in respect of Ta and Tb, are allowed to react with each other under dehydration condensation conditions, namely, in an inert solvent (for example, acetonitrile, dimethylformamide, methylene chloride, ethylene chloride or the like) in the presence of an appropriate catalyst (for example, N-hydroxysuccinimide, N,N'-dicyclohexylcarbodiimide, 1-hydroxybenzotriazole or the like), at a reaction temperature of from 0° C. to room temperature for 1 to 24 hours.

Also, in the case the bonding T is an ether bonding, the compound of interest can be obtained by a method in which an alkylamine having a halogen atom or an O-tosyl group (Ta) and a methoxypolyethylene glycol having a hydroxyl group (Tb) and treated with a hydride reagent such as sodium hydride, potassium hydride or the like, or the two compounds having the reverse relation in respect of Ta and Tb, are allowed to react with each other in an inert solvent (for example, dimethylformamide, tetrahydrofuran or the like) at a reaction temperature of from room temperature to 100° C. for 1 to 48 hours.

Also, in the case the bonding T is a urethane bonding, the compound of interest can be obtained by a method in which an alkylamine having an amino group (Ta) and a methoxypolyethylene glycol having a hydroxyl group (Tb) and converted to the corresponding isocyanate in a usual way (for example, treatment with 1,1-carbonyldiimidazole), or the two compounds having the reverse relation in respect of Ta and Tb, are allowed to react with each other in an inert solvent (for example, ether, tetrahydrofuran, 1,4-dioxane or the like) in the presence of an appropriate catalyst (for example, a base such as triethylamine, sodium bicarbonate or the like), at a reaction temperature of from 0C to room temperature for 0.5 to 24 hours.

Next, synthesis of the compounds of the general formula (II) can be effected, for example, as follows.

That is, in the case the bonding T is an acid amide bonding, the compound of interest can be obtained by a method in which an alkylamine having an amino group (Ta) and a polyethylene glycol having a carboxylic group (Tb), or the two compounds having the reverse relation in respect of Ta and Tb, are allowed to react with each other under dehydration condensation conditions, namely, in an inert solvent (for example, acetonitrile, dimethylformamide, methylene chloride, ethylene chloride or the like) in the presence of an appropriate catalyst (for example, N-hydroxysuccinimide, N,N'-dicyclohexylcarbodiimide, 1-hydroxybenzotriazole or the like), at a reaction temperature of from 0° C. to room temperature for 1 to 24 hours.

Also, in the case the bonding T is an ester bonding, the compound of interest can be obtained by a method in which an alkylamine having a hydroxyl group (Ta) and a polyethylene glycol having a carboxylic group (Tb), or the two compounds having the reverse relation in respect of Ta and Tb, are allowed to react with each other under dehydration condensation conditions, namely, in an inert solvent (for example, acetonitrile, dimethylformamide, methylene chloride, ethylene chloride or the like) in the presence of an appropriate catalyst (for example, N-hydroxysuccinimide, N,N'-dicyclohexylcarbodiimide, 1-hydroxybenzotriazole or the like), at a reaction temperature of from 0° C. to room temperature for 1 to 24 hours.

Also, in the case the bonding T is an ether bonding, the compound of interest can be obtained by a method in which an alkylamine having a halogen atom or an O-tosyl group (Ta) and a polyethylene glycol having a hydroxyl group and treated with a hydride reagent such as sodium hydride, potassium hydride or the like, or the two compounds having the reverse relation in respect of Ta and Tb, are allowed to react with each other in an inert solvent (for example, dimethylformamide, tetrahydrofuran or the like) at a reaction temperature of from room temperature to 100° C. for 1 to 48 hours.

Also, in the case the bonding T is a urethane bonding, the compound of interest can be obtained by a method in which an alkylamine having an amino group (Ta) and a polyethylene glycol having a hydroxyl group (Tb) and converted to the corresponding isocyanate in a usual way (for example, treatment with 1,1-carbonyldiimidazole), or the two compounds having the reverse relation in respect of Ta and Tb, are allowed to react with each other in an inert solvent (for example, ether, tetrahydrofuran, 1,4-dioxane or the like) in the presence of an appropriate catalyst (for example, a base such as triethylamine, sodium bicarbonate or the like), at a reaction temperature of from 0° C. to room temperature for 0.5 to 24 hours.

Next, synthesis of the compounds of the general formula (III) can be effected for example in the following manner.

That is, the compound of interest can be obtained by a method in which a branched type skeletal structure is first constructed making use of glutamic acid in accordance with the method disclosed in Japanese Patent Application Laid-Open (Kokai) No. Hei 5-202085, and then allowed at the carboxyl group of glutamic acid to react with the amino group of a triethylene glycol amine derivative of sugar whose sugar hydroxyl groups are protected with acetyl groups under dehydration condensation conditions, namely, in an inert solvent (for example, acetonitrile, dimethylformamide, methylene chloride, ethylene chloride or the like) in the presence of an appropriate catalyst (for example, N-hydroxysuccinimide, N,N'-dicyclohexylcarbodiimide, 1-hydroxybenzotriazole or the like), at a reaction temperature of from 0° C. to room temperature for 1 to 24 hours.

Next, synthesis of the compounds of the general formula (IV) can be effected for example in the following manner.

That is, the compound of interest can be obtained by the α-amino acid-N-carboxylic acid anhydride (hereinafter referred to as NCA) method, a homopolypeptide polymelization method, in which an amino acid NCA is allowed to undergo the reaction using an alkyldiamine compound as an initiator of which one of the amino groups is protected with a Z group, in an inert solvent (dioxane, tetrahydrofuran, benzene, nitrobenzene, dichloroethane, dimethylformamide or the like). By controlling concentrations of the initiator, the average chain length can be controlled.

Finally, synthesis of the alkylamine-introduced polysaccharides and modified products thereof can be effected for example in the following manner.

That is, the compound of interest can be obtained with reference to the method of the selective modification of the reducing end of dextran reported by M. Yalpani et al. (*J. Polym. Sci. Polym. Chem.*, 23, 1395–1405 (1985)), namely, by a method in which a polysaccharide such as dextran, pullulan, dextran sulfate, chondroitin sulfate or the like having an average molecular weight of 1 KDa to 100 KDa or a modified product thereof obtained by substituting the hydrogen atoms of some of its hydroxyl groups with carboxy $C_1$–$C_4$ alkyl groups, is added with both an alkyldiamine compound of which one of the amino groups is protected with a Fmoc group and sodium cyanoborohydride, both in excess amounts over the polysaccharide, in an appropriate solvent (for example, 0.1% acetic acid solution, its mixture with dimethylformamide or the like), and the mixture is incubated at a reaction temperature of from room temperature to 80° C. to effect reductive amination of the reducing end of the polysaccharide, followed by removing the protecting groups.

Reaction of each of these physiologically active proteins with each of these amino group donors in the presence of transglutaminase is, in short, effected under enzyme reaction conditions of transglutaminase, for example by incubating a physiologically active protein, an amino group donor and transglutaminase in an aqueous solvent having a pH value of from 6.0 to 8.0, more preferably around pH 7.5, at a temperature of from 25 to 40° C., more preferably around 37° C., for a period of 30 minutes to 2 hours. In this reaction, the concentration of the physiologically active protein may be preferably within the range of from 1 to 30 $\mu$M, and that of the amino group donor may be preferably within the range of from 100 $\mu$M to 30 mM. Preferably, concentration ratio of the physiologically active protein to the amino group donor may be within the range of from 1:100 to 1:5000, more preferably from 1:500 to 1:1000. In addition, transglutaminase may be used in an amount of from 0.1 to 10 units per 1 mmol of the protein.

The thus obtained physiologically active protein modified with an amino group donor can be separated and purified from the aqueous solvent by employing an appropriate combination of techniques known in the art, such as dialysis, gel filtration, ion exchange chromatography and the like.

The modified positions of any modified protein can be identified for example by carboxymethylating the Cys residues of a freeze-dried sample of the amino group donor-modified protein with monoiodoacetic acid in the presence of a denaturant, hydrolyzing the resultant product with an enzyme such as trypsin or the like, and then preparing a peptide map of the resultant peptides by a reversed phase HPLC or a capillary electrophoresis. On the other hand, a peptide map of the unmodified protein is prepared under the same conditions. The peptide peaks of both maps are compared to determine the modified peptide chain(s) and Gln residue(s).

BEST MODE FOR CARRYING OUT OF THE INVENTION

The following examples are provided to further illustrate the present invention.

EXAMPLE 1

Figure 1:
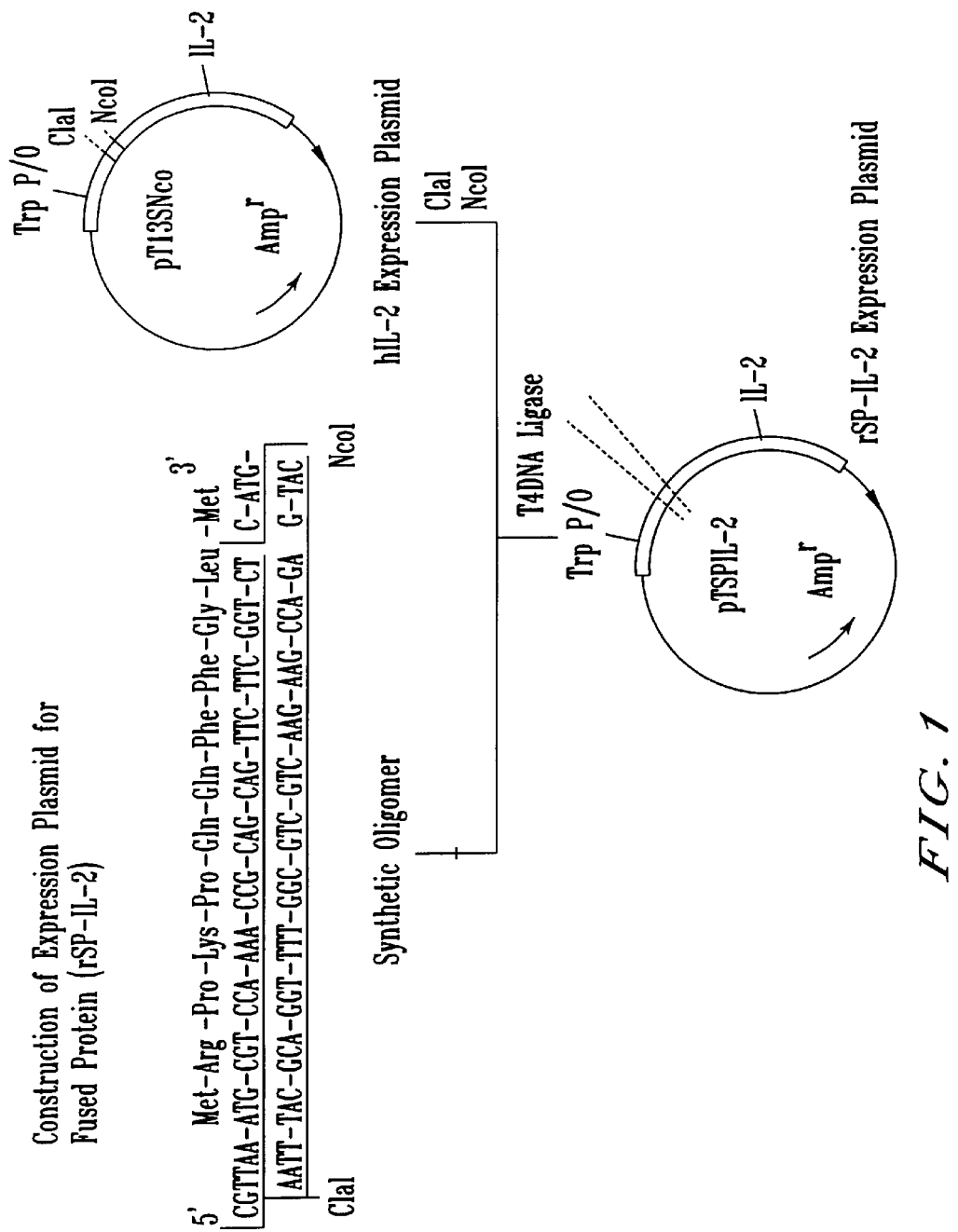
FIG. 1 is a graph showing the construction of a fused protein rSP-IL-2 expression plasmid pTSPIL-2 (Example 1).
Figure 2A:
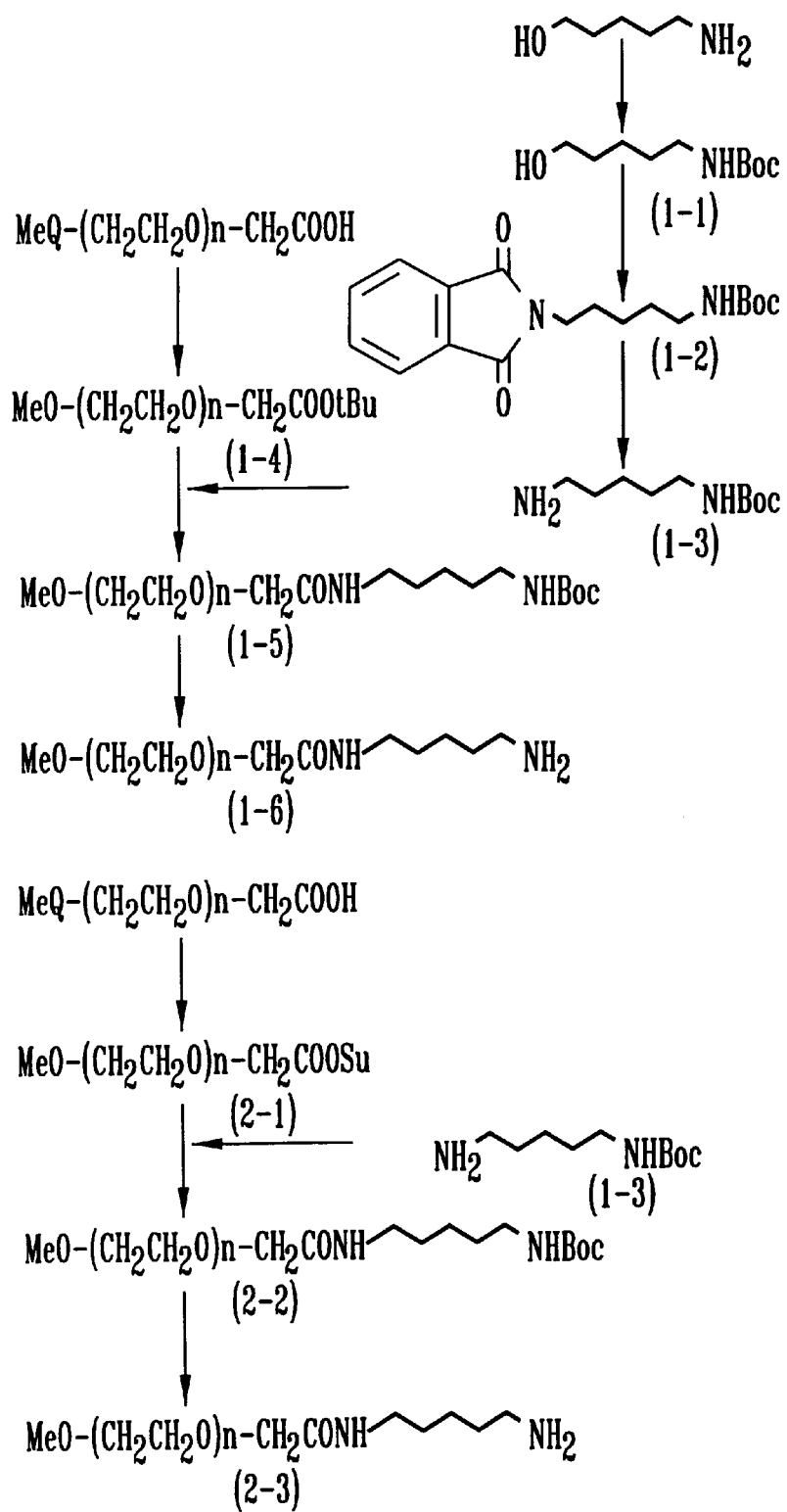
FIG. 2A is a graph showing the reactions involved in Example 7.
Figure 2B:
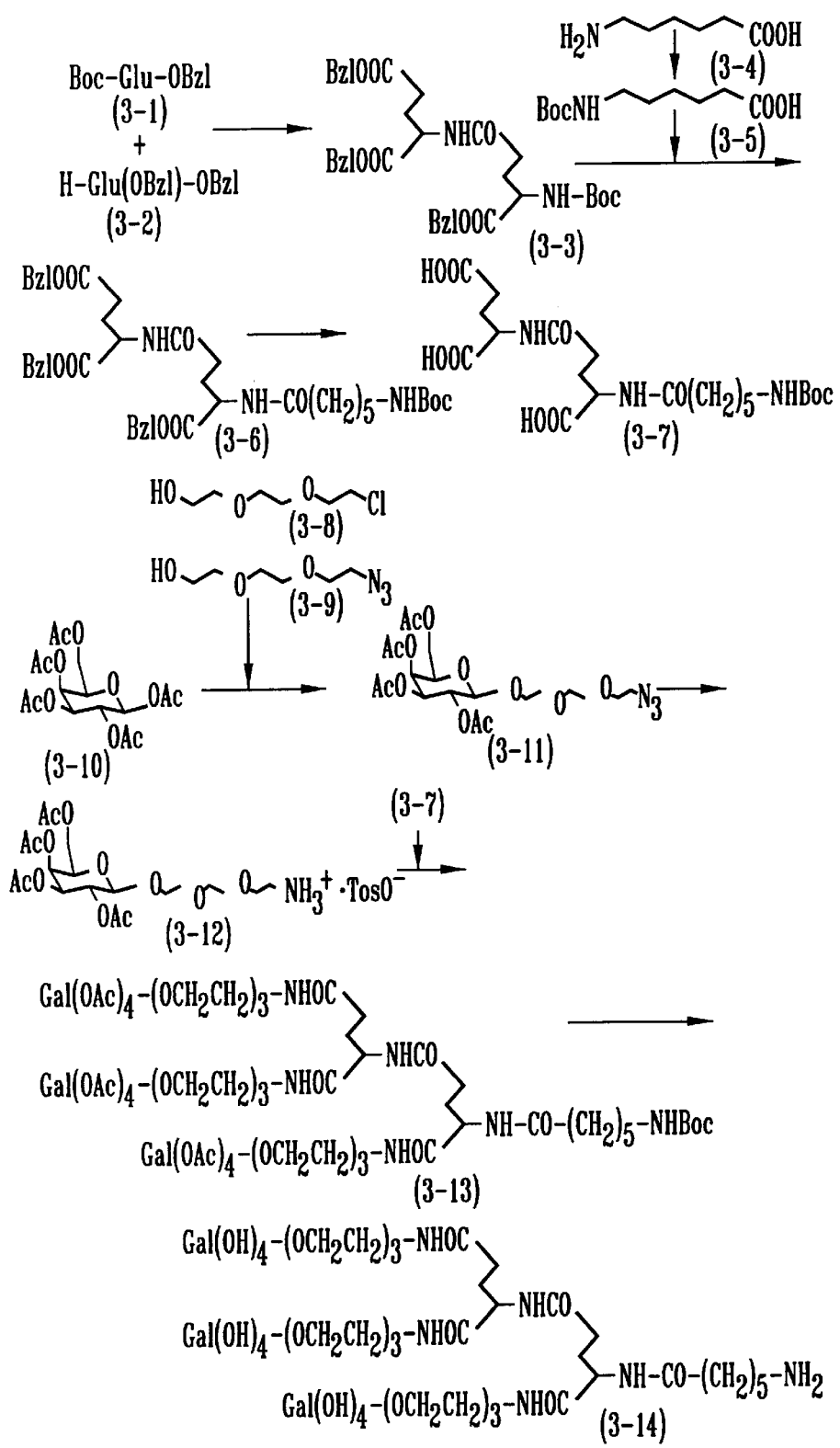
FIG. 2B is a graph showing the reactions involved in Example 7.
Figure 2C:
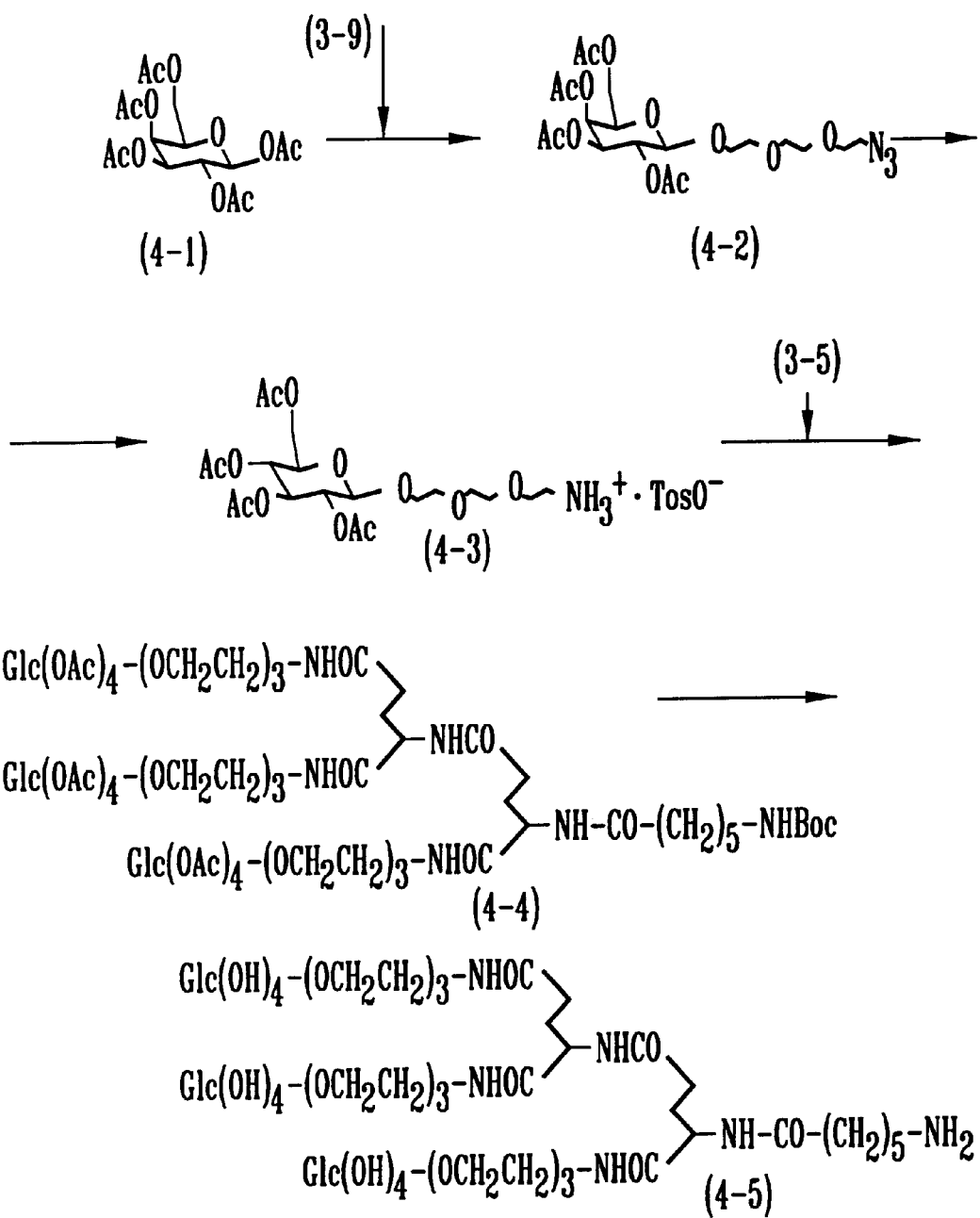
FIG. 2C is a graph showing the reactions involved in Example 7.
Figure 2D:
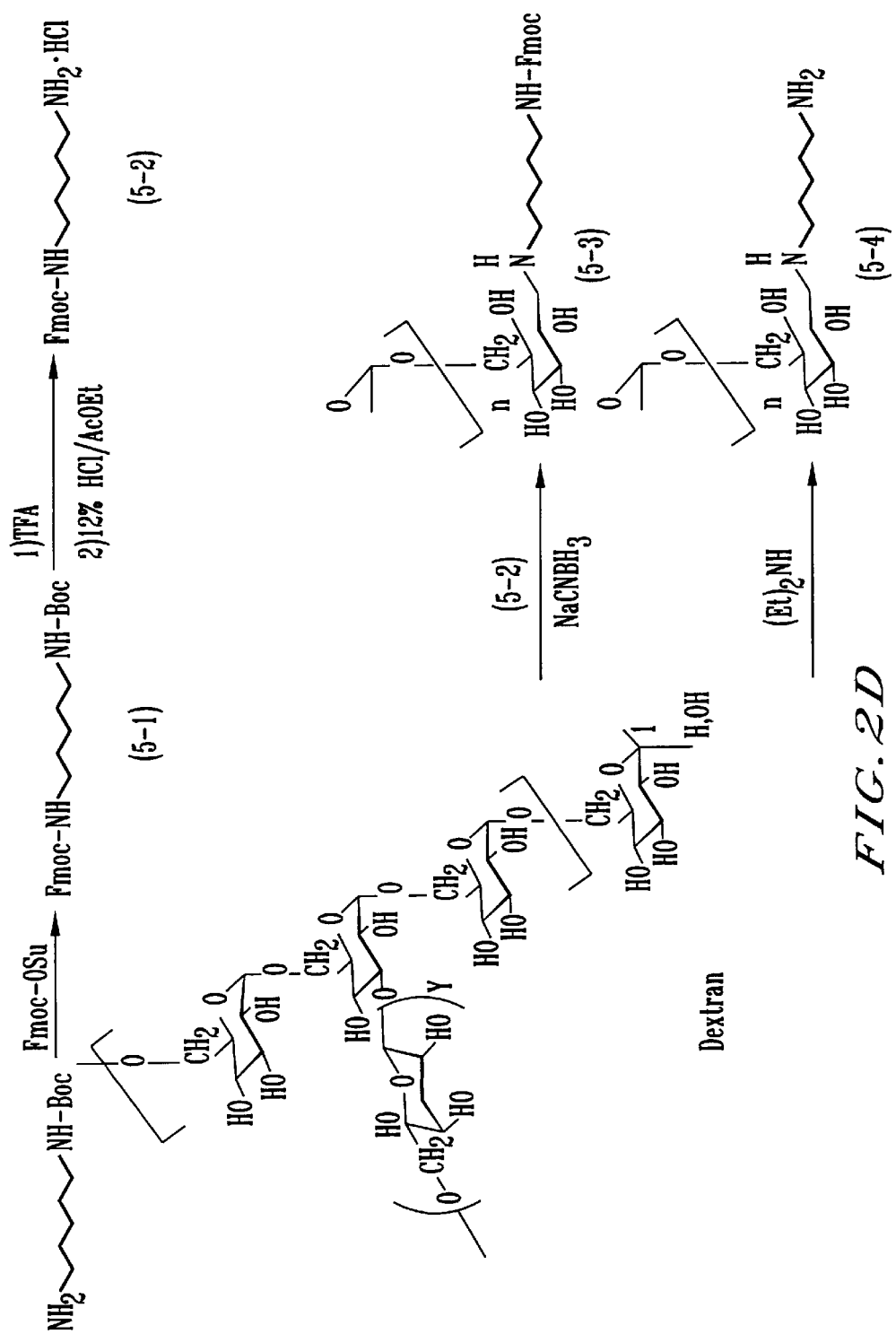
FIG. 2D is a graph showing the reactions involved in Example 7.
Figure 2E:
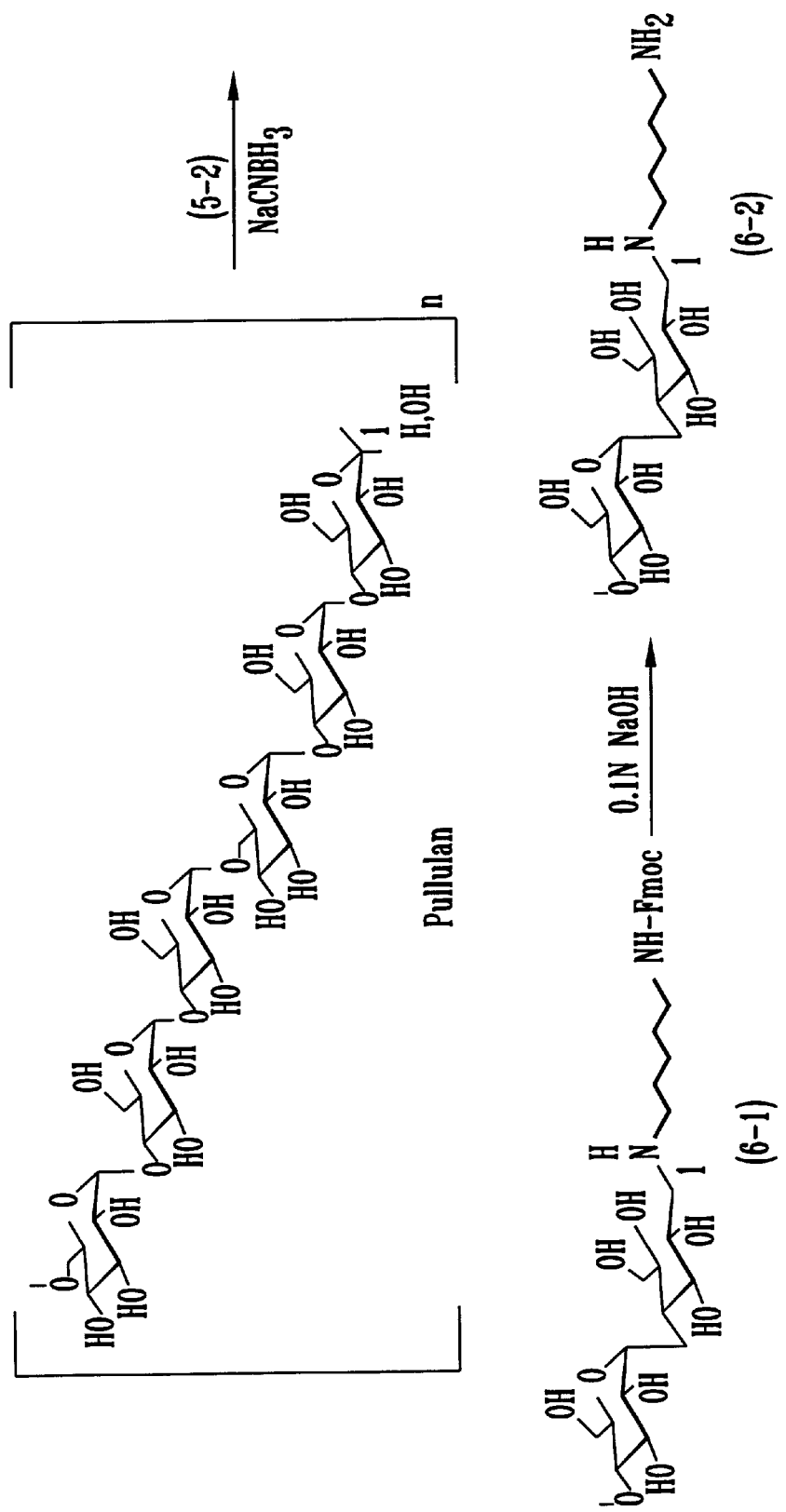
FIG. 2E is a graph showing the reactions involved in Example 7.

(Construction of plasmid pTSPIL-2 for direct expression of fused protein rSP-IL-2 and production thereof):

An expression plasmid pT13SNco (*E. coli* FERM P-10757) prepared by integrating hIL-2 cDNA into an expression vector containing a tryptophan promoter trp P/O was digested with restriction enzymes ClaI and NcoI, and, using T4 DNA ligase, the larger one of the resulting fragments was ligated with synthetic DNA fragments (5'CGTTAAATGCGTCCAAAACCGCAGCAGTTCTT CGGTCT3' (SEQ ID NO:32) and 5'CATGAGACCGAA GAACTGCTGCGGTTTTGGACGCATTTAA3') (SEQ ID NO:33) having a nucleotide sequence which encodes an amino acid sequence (Met-Arg-Pro-Lys-Pro-Gln-Gln-Phe-Phe-Gly-Leu) (SEQ ID NO:34) designed from a physiologically active peptide substance-P (SP) (cf. FIG. 1). A 15 ml portion of the resulting plasmid solution was gently mixed with 100 $\mu$l of an ice-cooled suspension of *E. coli* HB101 (ATCC 33694) competent cells, and the mixture was allowed to stand for 3 minutes in an ice bath and then subjected to heat treatment for 90 seconds in a water bath controlled at 42° C. Thereafter, the thus treated suspension was again allowed to stand for 2 minutes in the ice bath, added to 3 ml of 2×TY medium (1.6% trypton, 1% yeast extract and 0.5% NaCl), and then subjected to static culture at 30° C. for 60 minutes.

A 100 $\mu$l portion of the resulting culture broth was spread on LB agar medium (1% trypton, 0.5% yeast extract and 0.5% NaCl) plate which had been supplemented with ampicillin (100 $\mu$g/ml) and cultured overnight at 30° C. The ampicillin-resistant colonies formed by the culturing were picked up and again spread on the same ampicillin-containing agar plate to obtain an rSP-IL-2 producer strain (*E. coli* HB101/pTSPIL-2, which was first deposited under Accession No. FERM P-14369 on Jun. 14, 1994, and converted later to a Budapest Treaty international deposit under Accession No. FERM BP-5013 as of Feb. 23, 1995, in National Institute of Bioscience and Human Technology, Agency of Industrial Science and Technology, Japan). In this instance, the plasmid DNA was isolated and purified from the cells of the thus obtained strain and subjected to both restriction enzyme mapping and DNA nucleotide sequence analysis to confirm that the plasmid was the pTSPIL-2 of interest.

Production of rSP-IL-2 (i.e., a fused protein having the amino acid sequence of substance-P (SP) at the N-terminal of IL-2) was carried out in the following manner.

That is, the rSP-IL-2 producer strain (*E. coli* HB101/pTSPIL-2, i.e., *E. coli* FERM BP-5013) was cultured overnight at 28° C. on 2×TY medium, and a 10 ml portion of the culture broth was inoculated into 100 ml of M9 Casamino acid-mixted medium ($Na_2HPO_4$ 0.6%, $KH_2PO_4$ 0.3%, NaCl 0.05%, $NH_4Cl$ 0.1%, $MgSO_4$ 2 mM, glucose 0.2%, $CaCl_2$ 0.1 mM and Casamino acid 0.2%) containing ampicillin (100 $\mu$g/ml), L-leucine (200 $\mu$g/ml), L-proline (200 $\mu$g/ml) and thiamine hydrochloride (2.0 $\mu$g/ml) and subjected to shaking culture at 28° C. After 9 hours of the flask culture, indoleacrylic acid (IAA) was added to a final concentration of 25 $\mu$g/ml, and the culturing was continued at 31.5° C. for additional 14 hours.

When a portion of the culture broth was sampled and observed under a phase-contrast microscope (magnification, 1000 to 1500), inclusion bodies in the form of granules were found in thinly elongated *E. coli* cells. Thereafter, the culture broth was subjected to centrifugation (8000 rpm, 5 minutes) to collect the cells, which were subsequently frozen.

The thus collected cells were suspended in 20 mM Tris-HCl buffer (pH 8.0) containing 30 mM NaCl and subsequently added with egg lysozyme to a final concentration of 0.2 mg/ml. By 1 hour of standing in an ice bath, the cells were made into spheroplasts. Next, the cells were subjected to an ultrasonication treatment to take out the inclusion bodies. Subsequently, an insoluble fraction was obtained by centrifugation (6000 rpm, 15 minutes). To the insoluble fraction was added 10 mM of EDTA (pH 6.0), and the precipitates were suspended to make a suspension of recombinant SP-IL-2 (rSP-IL-2) inclusion bodies. A 20 mM Tris-HCl buffer (pH 8.0) containing 8 M guanidine hydrochloride was added to the thus prepared suspension in such an amount that the concentration of guanidine hydrochloride in the suspension was adjusted to 6 M, and the mixture was allowed to stand for 30 minutes at room temperature to solubilize the rSP-IL-2.

The thus solubilized rSP-IL-2 solution was adjusted to a protein concentration of 50 to 100 μg/ml with a 20 mM Tris-HCl buffer (pH 8.0) containing 10 mM of reduced type glutathione and 1 mM of oxidized type glutathione. The mixture was allowed to stand overnight at room temperature, whereby the stereostructure of the rSP-IL-2 was regenerated. In this instance, formation of intramolecular disulfide bonding from the denatured protein was confirmed by the shift in elution position of the protein using the reversed phase HPLC.

The solubilized rSP-IL-2 solution was applied onto a "Sephadex G-25" column which had been equilibrated in advance with a 50 mM acetic acid buffer (pH 6.0) and eluted with the same buffer. By monitoring the eluates by their absorbance at 280 nm, an eluate fraction of the fused protein free from the denaturant was obtained. The thus obtained eluate fraction was applied onto a "CM-Sepharose" column to effect adsorption of the rSP-IL-2 with a 50 mM acetic acid buffer (pH 6.0), the column was washed and then the protein was gradient-eluted by increasing the salt concentration to 500 mM at the same pH value. The above eluate fraction showing absorbance at 280 nm was purified using a "YMC-C$_8$AP" column (300×10 mm, manufactured by Yamamura Kagaku Co.), and then the buffer was exchanged with a preservative buffer, 50 mM acetic acid buffer (pH 5.0) containing 0.25 M of NaCl, using the "Sephadex G-25" column.

With respect to the purity of the thus purified product, SDS-PAGE analysis (using "Homogenious 20" gel) making use of "Phast System" (manufactured by Pharmacia) revealed that the purified product showed a band of only the main product among the proteins in the insoluble granules, and its molecular weight was larger than that of rhIL-2 (i.e., recombinant hIL-2) by about 1 KDa. In addition, when the N-terminal amino acid sequence of the purified product was analyzed by the Edman degradation, it was confirmed that the product had a structure in which the amino acid sequence of interest was added to the N-terminal side of the hIL-2. Protein concentration was calculated by defining the molar absorption coefficient of rSP-IL-2 at 280 nm as $1.2 \times 10^4$ M$^{-1}$ cm$^{-1}$ (protein recovery yield, about 20%).

EXAMPLE 2
(Construction of plasmid pTX1IL-2 for direct expression of fused protein rX1-IL-2 and production thereof):

In accordance with the procedure described in Example 1, the expression plasmid pT13SNco prepared by integrating hIL-2 cDNA into an expression vector containing a tryptophan promoter trp P/O was digested with restriction enzymes ClaI and NcoI, and, using T4 DNA ligase, the larger one of the resulting fragments was ligated with synthetic DNA fragments ($^{5'}$CGTTAAATGCGTCCAAA ACCTCAGCAGTT$^{3'}$ (SEQ ID NO:35) and $^{5'}$CATGAACTGCTGAGGTTTTGGACGCATTTAA$^{3'}$) (SEQ ID NO:36) having a nucleotide sequence which encodes Met-Arg-Pro-Lys-Pro-Gln-Gln-Phe-Met (SEQ ID NO:37). The thus obtained plasmid pTX1IL-2 was introduced into E. coli HB101 (ATCC 33694) to select ampicillin-resistant colonies. With respect to the thus selected colonies, restriction enzyme digestion analysis and determination of partial nucleotide sequences around the binding sites were carried out to select a pTX1IL-2-containing strain (E. coli HB101/pTX1IL-2, which was first deposited under Accession No. FERM P-14368 on Jun. 14, 1994, and converted later to a Budapest Treaty international deposit under Accession No. FERM BP-5012 as of Feb. 23, 1995, in National Institute of Bioscience and Human Technology, Agency of Industrial Science and Technology, Japan).

Production of recombinant X1-IL-2 (rX1-IL-2, i.e., a fused protein having the amino acid sequence of Met-Arg-Pro-Lys-Pro-Gln-Gln-Phe-Met (SEQ ID NO:37) at the N-terminal of IL-2) was also carried out in accordance with the procedure of Example 1. With respect to the purity of the purified product, SDS-PAGE analysis (using "Homogenious 20" gel) making use of "Phast System" (manufactured by Pharmacia) revealed that the purified product gave a band of protein only at the position corresponding to a molecular weight which was larger than that of rhIL-2 by about 0.5 KDa. In addition, when the N-terminal amino acid sequence of the purified product was analyzed by the Edman degradation, it was confirmed that the product had a structure in which the amino acid sequence of interest was added to the N-terminal side of the hIL-2. Protein concentration was calculated by defining the molar absorption coefficient of rX1-IL-2 at 280 nm as $1.2 \times 10^4$ M$^{-1}$ cm$^{-1}$ (protein recovery yield, about 20%).

EXAMPLE 3
(Construction of plasmid pTX2IL-2 for direct expression of fused protein rX2-IL-2 and production thereof):

In accordance with the procedure described in Example 1, the expression plasmid pT13SNco prepared by integrating hIL-2 cDNA into an expression vector containing a tryptophan promoter trp P/O was digested with restriction enzymes ClaI and NcoI, and, using T4 DNA ligase, the larger one of the resulting fragments was ligated with synthetic DNA fragments ($^{5'}$CGTTAAATGCCAAAACC TCAGCAGTT$^{3'}$ (SEQ ID NO:38) and $^{5'}$CATGAACTG CTGAGGTTTTGGCATTTAA$^{3'}$) (SEQ ID NO:39) having a nucleotide sequence which encodes Met-Pro-Lys-Pro-Gln-Gln-Phe-Met (SEQ ID NO:40). The thus obtained plasmid pTX2IL-2 was introduced into E. coli HB101 (ATCC 33694) to select ampicillin-resistant colonies. With respect to the thus selected colonies, restriction enzyme digestion analysis and determination of partial nucleotide sequences around the binding sites were carried out to select a pTX2IL-2-containing strain (E. coli HB101/pTX2IL-2, which was first deposited under Accession No. FERM P-14370 on Jun. 14, 1994, and converted later to a Budapest Treaty international deposit under Accession No. FERM BP-5014 as of Feb. 23, 1995, in National Institute of Bioscience and Human Technology, Agency of Industrial Science and Technology, Japan).

Production of recombinant X2-IL-2 (rX2-IL-2, i.e., a fused protein having the amino acid sequence of Met-Pro-Lys-Pro-Gln-Gln-Phe-Met (SEQ ID NO:40) at the N-terminal of IL-2) was also carried out in accordance with the procedure of Example 1. With respect to the purity of the purified product, SDS-PAGE analysis (using "Homogenious 20" gel) making use of "Phast System" (manufactured by Pharmacia) revealed that the purified product gave a band of protein only at the position corresponding to a molecular weight which was larger than that of rhIL-2 by about 0.5 KDa. In addition, when the N-terminal amino acid sequence of the purified product was analyzed by the Edman degradation, it was confirmed that the product had a structure in which the amino acid sequence of interest was added to the N-terminal side of the hIL-2. Protein concentration was calculated by defining the molar absorption coefficient of rX2-IL-2 at 280 nm as $1.2 \times 10^4$ $M^{-1}$ $cm^{-1}$ (protein recovery yield, about 20%).

EXAMPLE 4
(Construction of plasmid pTX3IL-2 for direct expression of fused protein rX3-IL-2 and production thereof):

In accordance with the procedure described in Example 1, the expression plasmid pT13SNco prepared by integrating hIL-2 cDNA into an expression vector containing a tryptophan promoter trp P/O was digested with restriction enzymes ClaI and NcoI, and, using T4 DNA ligase, the larger one of the resulting fragments was ligated with synthetic DNA fragments ($^{5'}$CGTTAAATGAAACCTCA GCAGTT$^{3'}$ (SEQ ID NO:41) and $^{5'}$CATGAACTGCTGAG-GTTTCATTTAA$^{3'}$ (SEQ ID NO:42)) having a nucleotide sequence which encodes Met-Lys-Pro-Gln-Gln-Phe-Met (SEQ ID NO:43). The thus obtained plasmid pTX3IL-2 was introduced into *E. coli* HB101 (ATCC 33694) to select ampicillin-resistant colonies. With respect to the thus selected colonies, restriction enzyme digestion analysis and determination of partial nucleotide sequences around the binding sites were carried out to select a pTX3IL-2-containing strain (*E. coli* HB101/pTX3IL-2, which was first deposited under Accession No. FERM P-14373 on Jun. 14, 1994, and later converted to a Budapest Treaty international deposit under Accession No. FERM BP-5017 as of Feb. 23, 1995, in National Institute of Bioscience and Human Technology, Agency of Industrial Science and Technology, Japan).

Production of recombinant X3-IL-2 (rX3-IL-2, i.e., a fused protein having the amino acid sequence of Met-Lys-Pro-Gln-Gln-Phe-Met (SEQ ID NO:43) at the N-terminal of IL-2) was also carried out in accordance with the procedure of Example 1. With respect to the purity of the purified product, SDS-PAGE analysis (using "Homogenious 20" gel) making use of "Phast System" (manufactured by Pharmacia) revealed that the purified product gave a band of protein only at the position corresponding to a molecular weight which was larger than that of rhIL-2 by about 0.5 KDa. In addition, when the N-terminal amino acid sequence of the purified product was analyzed by the Edman degradation, it was confirmed that the product had a structure in which the amino acid sequence of interest was added to the N-terminal side of the hIL-2. Protein concentration was calculated by defining the molar absorption coefficient of rX3-IL-2 at 280 nm as $1.2 \times 10^4$ $M^{-1}$ $cm^{-1}$ (protein recovery yield, about 20%).

EXAMPLE 5
(Construction of plasmid pTX4IL-2 for direct expression of fused protein rX4-IL-2 and production thereof):

In accordance with the procedure described in Example 1, the expression plasmid pT13SNco prepared by integrating hIL-2 cDNA into an expression vector containing a tryptophan promoter trp P/O was digested with restriction enzymes ClaI and NcoI, and, using T4 DNA ligase, the larger one of the resulting fragments was ligated with synthetic DNA fragments ($^{5'}$CGTTAAATGGCTCTGTGT GGCAGTTTCG$^{3'}$ (SEQ ID NO:44) and $^{5'}$CATGCGAAA CTGCCACAGAGCCATTTAA$^{3'}$) (SEQ ID NO:45) having a nucleotide sequence which encodes Met-Ala-Leu-Trp-Gln-Phe-Arg-Met (SEQ ID NO:46). The thus obtained plasmid pTX4IL-2 was introduced into *E. coli* HB101 (ATCC 33694) to select ampicillin-resistant colonies. With respect to the thus selected colonies, restriction enzyme digestion analysis and determination of partial nucleotide sequences around the binding sites were carried out to select a pTX4IL-2-containing strain (*E. coli* HB101/pTX4IL-2, which was first deposited under Accession No. FERM P-14371 on Jun. 14, 1994, and later converted to a Budapest Treaty international deposit under Accession No. FERM BP-5015 as of Feb. 23, 1995, in National Institute of Bioscience and Human Technology, Agency of Industrial Science and Technology, Japan).

Production of recombinant X4-IL-2 (rX4-IL-2, i.e., a fused protein having the amino acid sequence of Met-Ala-Leu-Trp-Gln-Phe-Arg-Met at the N-terminal of IL-2) was also carried out in accordance with the procedure of Example 1. With respect to the purity of the purified product, SDS-PAGE analysis (using "Homogenious 20" gel) making use of "Phast System" (manufactured by Pharmacia) revealed that the purified product gave a band of protein only at the position corresponding to a molecular weight which was larger than that of rhIL-2 by about 0.5 KDa. In addition, when the N-terminal amino acid sequence of the purified product was analyzed by the Edman degradation, it was confirmed that the product had a structure in which the amino acid sequence of interest was added to the N-terminal side of the hIL-2. Protein concentration was calculated by defining the molar absorption coefficient of rX4-IL-2 at 280 nm as $1.75 \times 10^4$ $M^{-1}$ $cm^{-1}$ (protein recovery yield, about 20%).

EXAMPLE 6
(Construction of plasmid pTX5IL-2 for direct expression of fused protein rX5-IL-2 and production thereof):

In accordance with the procedure described in Example 1, the expression plasmid pT13SNco prepared by integrating hIL-2 cDNA into an expression vector containing a tryptophan promoter trp P/O was digested with restriction enzymes ClaI and NcoI, and, using T4 DNA ligase, the larger one of the resulting fragments was ligated with synthetic DNA fragments ($^{5'}$CGTTAAATGGCTCAG CAGATCGT$^{3'}$ (SEQ ID NO:47) and $^{5'}$CATGAC GATCTGCTGAGCCATTTAA$^{3'}$) (SEQ ID NO:48) having a nucleotide sequence which encodes Met-Ala-Gln-Gln-Ile-Val-Met (SEQ ID NO:49). The thus obtained plasmid pTX5IL-2 was introduced into *E. Coli* HB101 (ATCC 33694) to select ampicillin-resistant colonies. With respect to the thus selected colonies, restriction enzyme digestion analysis and determination of partial nucleotide sequences around the binding sites were carried out to select a pTX5IL-2-containing strain (*E. coli* HB101/pTX5IL-2, which was first deposited under Accession No. FERM P-14372 on Jun. 14, 1994, and later converted to a Budapest Treaty international deposit under Accession No. FERM BP-5016 as of Feb. 23, 1995, in National Institute of Bioscience and Human Technology, Agency of Industrial Science and Technology, Japan).

Production of recombinant X5-IL-2 (rX5-IL-2, i.e., a fused protein having the amino acid sequence of Met-Ala-Gln-Gln-Ile-Val-Met at the N-terminal of IL-2) was also carried out in accordance with the procedure of Example 1. With respect to the purity of the purified product, SDS-PAGE analysis (using "Homogenious 20" gel) making use of "Phast System" (manufactured by Pharmacia) revealed that the purified product gave a band of protein only at the position corresponding to a molecular weight which was larger than that of rhIL-2 by about 0.5 KDa. In addition, when the N-terminal amino acid sequence of the purified product was analyzed by the Edman degradation, it was confirmed that the product had a structure in which the amino acid sequence of interest was added to the N-terminal side of the hIL-2. Protein concentration was calculated by defining the molar absorption coefficient of rX5-IL-2 at 280 nm as $1.2 \times 10^4$ $M^{-1}$ $cm^{-1}$ (protein recovery yield, about 20%).

EXAMPLE 7

Synthesis example

Reactions involved in this example are shown in FIG. 2A to FIG. 2E.

(a) Synthesis of Compound 1-1

5-Amino-1-pentanol (10 g) was dissolved in dichloromethane (60 ml), and added with an equivalent amount of N-methylmorpholine (9.03 ml). The mixture was cooled in an ice bath, and di-t-butylcarbonate (25.5 g) was added to the reaction solution, followed by stirring at room temperature for 24 hours. The reaction solution was diluted with dichloromethane, washed with water and dried, and then the solvent was removed by evaporation under reduced pressure. The resulting residue was purified by column chromatography (hexane-ethyl acetate, 3:2) using silica gel (150 g) to obtain Compound 1-1 (9.0 g) in the form of colorless oil.

IR ($CHCl_3$): 3456, 1708 $cm^{-1}$.

$^1$H-NMR ($CDCl_3$) δ: 3.65 (2H, t, J=6.5 Hz), 3.16–3.08 (2H, m), 1.64–1.56 (2H, m), 1.54–1.46 (2H, m), 1.44 (9H, s), 1.43–1.35 (2H, m).

(b) Synthesis of Compound 1-2

In an atmosphere of argon gas, Compound 1-1 (5.0 g) was dissolved in dry tetrahydrofuran (100 ml), and subsequently added with phthalimide (3.8 g), and the mixture was cooled in an water bath. To the reaction solution were added triphenylphosphine (7.7 g) and diisopropyl azodicarboxylate (5.8 ml), followed by 12 hours of stirring at room temperature. The reaction solution was diluted with chloroform, and the solvent was removed by distillation under reduced pressure. The resulting residue was purified by column chromatography (toluene-ethyl acetate, 10:1) using silica gel (450 g) to obtain Compound 1-2 (8.4 g) in the form of white powder.

IR (KBr): 3354, 1776, 1722, 1674, 723 $cm^{-1}$.

$^1$H-NMR ($CDCl_3$) δ: 7.85–7.83 (2H, m),$_1$ 7.72–7.70 (2H, m), 3.69 (2H, t, J=7.2 Hz), 3.14–3.06 (2H, m)), 1.74–1.66 (2 H, m), 1.57–1.49 (2H, m).

(c) Synthesis of Compound 1-3

Compound 1-2 (4.0 g) was dissolved in dry ethanol (32 ml) and refluxed under cooling condition. To the reaction solution was added hydrazine hydrate (0.83 ml), followed by 6 hours of reflux. After cooling, the precipitates were filtered and the filtrate was concentrated by distillation under reduced pressure. Chloroform and 1 N sodium hydroxide were added to the resulting residue, the mixture was washed with water and dried, and then the solvent was removed by distillation under reduced pressure to obtain Compound 1-3 (2.45 g) in the form of light yellow oil.

IR ($CHCl_3$): 3456, 1708 $cm^{-1}$.

$^1$H-NMR ($CDCl_3$) δ: 3.35–3.05 (2H, m), 2.69 (2H, t, J=7.0 Hz), 1.55–1.30 (6H, m)), 1.44 (9H, s).

(d) Synthesis of Compounds 1-4 and 1-5

α-Carboxymethyl-ω-methoxypolyoxyethylene (5 g, average molecular weight 5000, manufactured by Nippon Oil & Fats Co.) was dissolved in dry dichloromethane (25 ml). To the solution were subsequently added 1-hydroxybenzotriazole (0.175 g) and dicyclohexylcarbodiimide (0.289 g) in this order, followed by 12 hours of stirring at room temperature in an atmosphere of argon gas to effect formation of Compound 1-4. Without isolating the Compound 1-4, the reaction solution was mixed with Compound 1-3 (0.5 g) and stirred for 12 hours at room temperature in an atmosphere of argon gas. The solvent was removed by distillation under reduced pressure, and the resulting residue was purified by column chromatography (dichloromethane-methanol-water, 10:3:1) using silica gel (450 g) to obtain Compound 1-5 (1.94 g) in the form of white powder.

IR (KBr): 3527, 2883, 1114 $cm^{-1}$.

$^1$H-NMR ($CDCl_3$) δ: 3.98 (2H, s), 3.72–3.59 (559H, m), 3.38 (3H, s), 3.31–3.26 (2H, m), 3.14–3.07 (2H, m), 1.56–1.30 (6H, m), 1.44 (9H, s).

(e) Synthesis of Compound 1-6

Compound 1-5 (1.72 g) was dissolved in trifluoroacetic acid (7 ml), followed by 12 hours of stirring at room temperature. After the reaction solution was concentrated under reduced pressure, the resulting residue was added with methanol and neutralized with sodium methoxide. After the reaction solution was concentrated again under reduced pressure, the resulting residue was purified by column chromatography (dichloromethane-methanol-water, 10:3:1) using silica gel (450 g) to obtain Compound 1-6 (3.7 g) in the form of white powder.

IR ($CHCl_3$): 2880, 1681, 1140, 1099 $cm^{-1}$.

$^1$H-NMR ($CDCl_3$) δ: 4.08 (2H, s), 3.74–3.59 (545H, m), 3.39 (3H, s), 3.34–3.28 (2H, m), 3.02–2.94 (2H, m), 1.62–1.55 (2H, m), 1.29–1.22 (2H, m).

(f) Synthesis of Compounds 2-1 and 2-2

α-Carboxymethyl-ω-methoxypolyoxyethylene (5 g, average molecular weight 10000, manufactured by Nippon Oil & Fats Co.) was dissolved in dry dimethylformamide (8 ml). To the solution were subsequently added N-hydroxysuccinimide (0.075 g) and dicyclohexylcarbodiimide (0.13 g) in this order, followed by 12 hours of stirring at room temperature in an atmosphere of argon gas to effect formation of Compound 2-1. Without isolating the Compound 2-1, the reaction solution was mixed with Compound 1-3 (0.22 g) and stirred for 12 hours at room temperature in an atmosphere of argon gas. The solvent was removed by distillation under reduced pressure, and the resulting residue was purified by column chromatography (dichloromethane-methanol-water, 10:3:1) using silica gel (450 g) to obtain Compound 2-2 (3.7 g) in the form of white powder.

IR ($CHCl_3$): 3440, 2895, 1109 $cm^{-1}$.

$^1$H-NMR ($CDCl_3$) δ: 3.98 (2H, s), 3.74–3.58 (1036H, m), 3.38 (3H, s), 3.32–3.24 (2H, m), 3.16–3.06 (2H, m), 1.56–1.26 (6H, m), 1.44 (9H, s).

(g) Synthesis of Compound 2-3

Compound 2-2 (0.69 g) was dissolved in trifluoroacetic acid (6 ml), followed by 12 hours of stirring at room temperature. After the reaction solution was concentrated under reduced pressure, the resulting residue was added with methanol and neutralized with sodium methoxide. After the reaction solution was again concentrated under reduced pressure, the resulting residue was purified by column chromatography (dichloromethane-methanol-water, 10:3:1) using silica gel (120 g) to obtain Compound 2-3 (0.56 g) in the form of white powder.

IR ($CHCl_3$): 2880, 1679, 1138, 1097 $cm^{-1}$.

$^1$H-NMR ($CDCl_3$) δ: 4.03 (2H, s), 3.76–3.52 (1000H, m), 3.38 (3H, s), 3.33–3.27 (2H, m), 3.01–2.95 (2H, m), 1.56–1.30 (6H, m).

(h) Synthesis of Compound 3-3

Boc-Glu-OBzl (Compound 3-1, 4.98 g) and N-methylmorpholine (1.62 ml) were dissolved in tetrahydrofuran (100 ml), and the resulting solution was cooled with methanol-dry ice, added with ethyl chlorocarbonate (1.4 ml), stirred at −30° C. for 5 minutes, cooled again to −40° C. or lower, and then further mixed with a dimethylformamide solution (50 ml) containing H-Glu(OBzl)-OBzl.TosOH (Compound 3-2, 7.38 g) and N-methylmorpholine (1.62 ml). After removing the cooling medium, the resulting mixture was stirred overnight with cooling with sodium chloride and ice. The reaction solution was filtered through celite, and the filtrate was concentrated. The resulting residue was dissolved in ethyl acetate, the solution was washed with aqueous 10% citric acid solution, saturated brine and aqueous 10% sodium bicarbonate solution, and then the resulting organic layer was dried on magnesium sulfate. The resulting solution was filtered, and the solvent was distilled off to obtain 9 g of a solid substance. By recrystallizing the solid substance from ethyl acetate/methanol, 8.1 g (85%) of the title compound was obtained.

$[\alpha]_D$=+16.10 (c=0.93, chloroform)

IR (chloroform) cm$^{-1}$: 1738, 1500, 1166.

$^1$H-NMR (CDCl$_3$) δ: 7.2–7.3 (15H, m), 6.41 (1H, d, J=7.0 Hz), 5.25 (1H, d, J=7.0 Hz), 5.0–5.2 (6H, m), 4.62–4.64 (1H, m), 4.30–4.35 (1H, m), 2.3–2.5 (2H, m), 2.1–2.25 (4H, m), 1.98–2.06 (1H, m), 1.86–1.94 (1H, m), 1.4 (9H, s).

(i) Synthesis of Compound 3-5

6-Aminohexanoic acid (Compound 3-4, 10 g) was dissolved in dioxane-water (2:1) (200 ml). To the solution, while cooling in an ice bath, were added 1 N sodium hydroxide solution (70 ml) and di-t-butylcarbonate (18.3 g), followed by overnight stirring at room temperature. After removing the solvent by distillation, the resulting residue was adjusted to pH 2 with 1 N hydrochloric acid and extracted with dichloromethane. The resulting organic layer was dried on magnesium sulfate and filtered, and then the solvent was removed by distillation to obtain the compound of interest (3-5, 16.5 g) in the form of white solid.

IR (chloroform) cm$^{-1}$: 1710, 1510, 1166.

$^1$H-NMR (CDCl$_3$) δ: 3.15–3.05 (2H, br), 2.36 (2H, t, J=7.5 Hz), 1.66 (2H, dt, J=15 Hz, J=7.5 Hz), 1.50 (2H, dt, J=15 Hz, J=7.5 Hz), 1.44 (9H, s), 1.42–1.34 (2H, m)

(j) Synthesis of Compound 3-6

Compound 3-3 (2.0 g) was dissolved in trifluoroacetic acid (5 ml) and allowed to stand for 3 hours. The solvent was removed by distillation, and the resulting residue was subjected twice to azeotropic distillation treatment with ethanol. The thus obtained residue was dissolved in 5 ml of methanol and neutralized with N-methylmorpholine (330 μl). The solvent was removed by distillation, and the resulting residue was dissolved in dichloromethane (50 ml). This will be referred to as Solution A. With cooling in an ice bath, Compound 3-5 (700 mg), dicyclohexylcarbodiimide (680 mg) and N-hydroxysuccinimide (380 mg) were dissolved in dichloromethane (50 ml), and added with Solution A, followed by overnight stirring at 5° C. The reaction solution was diluted with dichloromethane (100 ml), washed with aqueous 10% citric acid solution, saturated brine and aqueous 10% sodium carbonate solution, dried on magnesium sulfate, and then filtered, followed by distillation removal of the solvent. The resulting residue was purified by silica gel column chromatography (hexane: ethyl acetate=1:1–1:2) to obtain Compound 3-6 (800 mg) in the form of white solid.

$[\alpha]_D$=−3.320 (c=1.08, chloroform).

IR (chloroform) cm$^{-1}$: 1738, 1682, 1645, 1537, 1169.

$^1$H-NMR (CDCl$_3$) δ: 7.3–7.4 (15H, m), 6.5–6.6 (2H, br), 5.06–5.20 (6H, m), 4.55–4.65 (3H, m), 3.06–3.10 (2H, m), 2.34–2.48 (2H, m), 2.13–2.26 (6H, m), 1.93–2.06 (2H, m), 1.60–1.64 (2H, m), 1.39–1.48 (11H, m), 1.30–1.34 (2H, m).

(k) Synthesis of Compound 3-7

Compound 3-6 (500 mg) was dissolved in tetrahydrofuran (20 ml) and ethyl acetate (20 ml), 10% palladium-carbon (100 mg) was added to the solution, and then the mixture was stirred overnight under 1 hydrogen atmospheric pressure. By subjecting the reaction mixture to filtration and removing by distillation the solvent, the title Compound (400 mg) was obtained in the form of solid.

$^1$H-NMR (CD$_3$OD) δ: 4.44 (1H, dd, J=5.0 Hz, J=9.0 Hz), 4.39 (1H, dd, J=5.0 Hz, J=9.0 Hz), 3.03 (2H, t, J=7.0 Hz), 2.35–2.43 (4H, m), 2.26 (2H, t, J=7.5 Hz), 2.15–2.24 (2H, m), 1.91–2.0 (2H, m), 1.61–1.67 (2H, m), 1.34–1.52 (13H, m).

(l) Synthesis of Compound 3-9

Dimethylformamide (50 ml) was added to [2-(2-chloroethoxy)ethoxy]ethanol (2.9 g) and sodium azide (3.4 g), and the mixture was stirred overnight at 80° C. The solvent was removed by distillation, and the resulting residue was purified by silica gel column chromatography (dichloromethane) to obtain 2.5 g of the title compound (3-9) in the form of oil.

$^1$H-NMR (CDCl$_3$) δ: 3.73–3.76 (2H, m), 3.67–3.71 (6H, m), 3.61–3.63 (2H, m), 3.40 (2H, t, J=5.0 Hz), 2.33 (1H, s)

(m) Synthesis of Compound 3-11

β-D-Galactopyranose pentaacetate (3-10) (10 g) and Compound 3-9 (9.0 g) were dissolved in dichloromethane (100 ml), and the mixture was subsequently added with boron trifluoride ether complex salt (6.3 ml), followed by overnight stirring. The reaction mixture was diluted with dichloromethane (500 ml) and washed with an aqueous saturated sodium bicarbonate solution, and the resulting organic layer was dried on magnesium sulfate. After filtration and distillation removal of the solvent, the resulting residue was applied onto a silica gel column chromatography and eluted with hexane:ethyl acetate=3:1 to 1:1 to obtain a mixture of the product and alcohol compound. To this were added acetic anhydride (2 ml) and pyridine (20 ml), followed by overnight stirring. The solvent was removed by distillation, the resulting residue was dissolved in ethyl acetate and washed with 0.5 N hydrochloric acid, saturated brine and aqueous saturated sodium bicarbonate solution, and then the resulting organic layer was dried on magnesium sulfate. After filtration and distillation removal of the solvent, the resulting residue was applied onto a silica gel column chromatography and eluted with hexane:ethyl acetate=3:1 to 1:1 to obtain 7.4 g (55%) of the title compound in the form of oil.

$[\alpha]_D$=−6.29° (c=1.05, chloroform).

IR (chloroform) cm$^{-1}$: 2110, 1749, 1369.

$^1$H-NMR (CDCl$_3$) δ: 5.39 (1H, d, J=3.5 Hz), 5.21 (1H, dd, J=8.0 Hz, J=10.5 Hz), 5.02 (1H, dd, J=3.5 Hz, J=10.5 Hz), 4.58 (1H, d, J=8.0 Hz), 4.10–4.20 (2H, m), 3.89–3.99 (2 H, m), 3.74–3.78 (1H, m)), 3.64–3.69 (8H, m), 3.40 (2H, t, J=5.0 Hz), 2.15 (3H, s), 2.06 (3H, s), 2.05 (3H, s), 1.99 (3H, s).

(n) Synthesis of Compound 3-13

Compound 3-11 (2.3 g) and p-toluenesulfonic acid (850 mg) were dissolved in ethanol (50 ml), Lindlar catalyst (1.0 g) was added to the solution, and then the mixture was shaken for 1 hour under a pressure of hydrogen (50 psi). Thereafter, Lindlar catalyst (1.0 g) was further added to the mixture, and the mass was shaken for 1 hour under a pressure of hydrogen (50 psi). The catalyst was removed by filtration and the solvent was distilled off. The resulting residue was dissolved in acetonitrile (10 ml) and neutralized with N-methylmorpholine (500 μl). This will be referred to as Solution A.

Compound 3-7 (700 mg) was dissolved in dimethylformamide (10 ml) and added, with cooling in an ice bath, with N-hydroxysuccinimide (510 mg) and dicyclohexylcarbodiimide (920 mg), and the mixture was stirred overnight at 4° C. The reaction solution was concentrated, the resulting residue was dissolved in ethyl acetate and washed with aqueous 10% citric acid solution, saturated brine and aqueous 10% sodium bicarbonate solution, and then the resulting organic layer was dried on magnesium sulfate. After filtration, the solvent was removed by distillation. The thus obtained residue was applied onto a silica gel column chromatography and eluted by changing the eluents from dichloromethane to dichloromethane:methanol=30:1, and then to 25:1, thereby obtaining 1.8 g of the title compound in the form of powder.

$[\alpha]_D$=−11.20 (c=1.00, chloroform).

IR (KBr) cm$^{-1}$: 1753, 16339, 1371, 1226.

$^1$H-NMR (CDCl$_3$) δ: 7.80–7.85 (1H, m), 7.24–7.26 (1H, m), 7.12–7.18 (1H, m), 7.04–7.08 (1H, m), 6.58–6.62 (1H, m), 5.39 (3H, d, J=3.5 Hz), 5.17–5.22 (3H, m), 5.02–5.06 (3H, m, H-2), 4.72–4.76 (1H, m), 4.55–4.57 (3H, m), 4.38–4.43 (2H, m), 4.10–4.20 (6H, m), 3.93–3.98 (6H, m), 3.70–3.75 (6H, m), 3.5–3.6 (34H, m), 3.8–3.12 (2H, m), 2.2–2.4 (2H, m), 2.09 (9H, s), 2.04 (9H, s), 2.02 (9H, s), 2.01 (9H, s), 1.60–1.66 (2H, m), 1.46–1.52 (2H, m), 1.42 (9H, s), 1.30–1.36 (2H, m).

(o) Synthesis of Compound 3-14

Compound 3-13 (2.4 g) was dissolved in 50% trifluoroacetic acid-dichloromethane solution, stirred for 1 hour and, after distilling off the solvent, subjected twice to azeotropic distillation with ethanol. The resulting residue was dissolved in methanol (30 ml), neutralized with a 28% sodium methoxide-methanol solution, and then purified by a silica gel column chromatography (dichloromethane:methanol= 30:1→5:1). The thus obtained powder was dissolved in methanol (20 ml) and added, with cooling in an ice bath, with a 28% sodium methoxide-methanol solution (200 μl), and, when the addition was completed, the resulting mixture was warmed to room temperature and stirred for 1 hour. By neutralizing with an anion exchange resin Dowex 50W (H$^+$), removing the resin, and then distilling off the solvent, 500 mg of the title compound was obtained in the form of powder.

$[\alpha]_D$=−5.710 (c=0.63, methanol).

$^1$H-NMR (CD$_3$OD) δ: 4.8–4.9 (11H, m), 4.34–4.36 (1H, m), 4.29–4.31 (1H, m), 4.26–4.29 (3H, m), 4.08–4.05 (3H, m), 3.83–3.85 (2H, m), 3.72–3.79 (6H, m), 3.68–3.72 (5 H, m), 3.65–3.68 (5H, m), 3.61–3.64 (5H, m), 3.48–3.59 (5H, m), 3.36–3.40 (1H, m), 3.26–3.32 (36H, m), 2.9–3.0 (2H, m), 2.25–2.40 (6H, m), 2.03–2.10 (1H, m), 1.86–1.98 (1H, m), 1.60–1.70 (1H, m).

(p) Synthesis of Compound 4-2

β-D-Glucopyranose pentaacetate (10 g) and 2-[2-(azidoethoxy]ethoxylethanol (3-9) (9 g) were dissolved in dichloromethane (100 ml). To the solution was subsequently added boron trifluoride ether complex salt (6.3 ml), followed by overnight stirring. The reaction mixture was diluted with dichloromethane (500 ml) and washed with aqueous saturated sodium bicarbonate solution, and the resulting organic layer was dried on magnesium sulfate. After filtration and distillation removal of the solvent, the resulting residue was applied onto a chromatography and eluted with hexane:ethyl acetate=3:1 to 1:1 to obtain a mixture of the product and alcohol compound. To this were added acetic anhydride (2 ml) and pyridine (20 ml), followed by overnight stirring. The solvent was removed by distillation, the resulting residue was dissolved in ethyl acetate and washed with 0.5 N hydrochloric acid, saturated brine and aqueous saturated sodium bicarbonate solution, and then the resulting organic layer was dried on magnesium sulfate. After filtration and distillation removal of the solvent, the resulting residue was applied onto silica gel column chromatography and eluted with hexane:ethyl acetate=3:1 to 1:1 to obtain Compound 4-2 (5.9 g, 44%) in the form of oil.

$[\alpha]_D$=−15.20 (c=0.97, chloroform).

IR (chloroform) cm$^{-1}$: 2110, 1755, 1367.

$^1$H-NMR (CDCl$_3$) δ: 5.21 (1H, t, J=9.5 Hz), 5.09 (1H, t, J=9.5 Hz), 5.00 (1H, dd, J=8.0 Hz, J=9.5 Hz), 4.61 (1H, d, J=8.0 Hz), 4.26 (1H, dd, J 4.5 Hz, 12.0 Hz), 4.14 (1H, dd, J=2.5 Hz, J=12 Hz), 3.93–3.97 (1H, m), 3.73–3.78 (1H, m), 3.64–3.73 (9H, m), 3.40 (2H, t, J=5.0 Hz), 2.09 (3H, s), 2.05 (3H, s), 2.03 (3H, s), 2.01 (3H, s).

(q) Synthesis of Compound 4-4

Compound 4-2 (2.3 g) and p-toluenesulfonic acid (850 mg) were dissolved in ethanol (50 ml), Lindlar catalyst (1.0 g) was added to the solution, and then the mixture was shaken for 1 hour under a pressure of hydrogen (50 psi). Thereafter, Lindlar catalyst (1.0 g) was again added to the mixture, and the mixture was shaken for 1 hour under a pressure of hydrogen (50 psi). The catalyst was removed by filtration, and the solvent was distilled off. The resulting residue was dissolved in acetonitrile (10 ml) and neutralized with N-methylmorpholine (500 μl). This will be referred to as Solution A.

Compound 3-7 (700 mg) was dissolved in dimethylformamide (10 ml). To the solution, with cooling in an ice bath, were added N-hydroxysuccinimide (510 mg) and dicyclohexylcarbodiimide (920 mg), and the mixture was stirred overnight at 4° C. and then added with Solution A with ice cooling, followed by stirring overnight at 4° C. The reaction solution was concentrated, the resulting residue was dissolved in ethyl acetate and washed with aqueous 10% citric acid solution, saturated brine and aqueous 10% sodium carbonate solution, and then the resulting organic layer was dried on magnesium sulfate. After filtration, the solvent was removed by distillation. The thus obtained residue was applied onto a silica gel column chromatography and eluted by changing the eluents from dichloromethane to dichloromethane:methanol=30:1, and then to 25:1, thereby obtaining 1.6 g of the title Compound in the form of powder.

$^1$H-NMR (CDCl$_3$) δ: 7.75–7.80 (1H, m), 7.37–7.41 (1H, m), 7.18 (1H, d, J=7.5 Hz), 7.0–7.04 (1H, m), 5.46–5.49 (1 H, d, J=8 Hz), 5.19–5.24 (3H, m), 5.06–5.12 (3H, m), 4.96–5.02 (3H, m), 4.59–4.61 (3H, m), 4.38–4.43 (2H, m), 4.10–4.20 (6H, m), 3.93–3.98 (6H, m), 3.70–3.75 (6 H, m), 3.5–3.6 (34H, m), 3.8–3.12 (2H, m), 2.2–2.4 (2H, m), 2.09 (9H, s), 2.04 (9H, s), 2.02 (9H, s), 2.01 (9H, s), 1.60–1.66 (2H, m), 1.46–1.52 (2H, m), 1.42 (9H, s), 1.30–1.36 (2H, m).

(r) Synthesis of Compound 4-5

Compound 4-4 (5.4 g) was dissolved in 50% trifluoroacetic acid-dichloromethane solution, stirred for 1 hour and, after distilling off the solvent, subjected twice to azeotropic distillation with ethanol. The resulting residue was dissolved in methanol (30 ml), neutralized with a 28% sodium methoxide-methanol solution, and then purified by silica gel column chromatography (dichloromethane:methanol= 30:1→5:1). The thus obtained powder was dissolved in methanol (20 ml). To the solution, with cooling in an ice bath, was subsequently added with a 28% sodium methoxide-methanol solution (200 μl), and, when the addition was completed, the resulting mixture was warmed to room temperature and stirred for 1 hour. By neutralizing with an anion exchange resin Dowex (DOWEX® 50W (H⁺), removing the resin, and then distilling off the solvent, 500 mg of the title Compound was obtained in the form of powder.

$[\alpha]_D = -13.7°$ (c=0.19, methanol).

¹H-NMR (CD₃OD) δ: 4.8–4.9 (11H, m), 4.34–4.36 (1H, m), 4.26–4.40 (3H, m), 4.01–4.05 (2H, m), 3.83–3.85 (2H, m), 3.72–3.79 (7H, m), 3.68–3.72 (5H, m), 3.65–3.68 (5H, m), 3.61–3.64 (5H, m), 3.48–3.59 (5H, m), 3.36–3.40 (1H, m), 3.26–3.32 (37H, m), 2.9–3.0 (1H, m), 2.25–2.40 (5H, m), 2.03–2.10 (1H, m), 1.86–1.98 (1H, m), 1.60–1.70 (2H, m).

(s) Synthesis of Compound 5-1

With cooling in an ice bath, 3 g of N-Boc-1,5-diaminopentane was dissolved in 57 ml of dichloromethane. The solution was subsequently added with 5.49 g of Fmoc-OSu, followed by 2 hours of stirring at room temperature. After removing the solvent by distillation, the resulting residue was purified by silica gel column chromatography (dichloromethane:methanol=50:1) to obtain 4.5 g of the title compound in the form of white powder.

¹H-NMR (CDCl₃) δ: 7.77–7.76 (2H, d), 7.60–7.59 (2H, d), 7.42–7.39 (2H, t), 7.33–7.30 (2H, t), 4.23–4.20 (2H, m), 3.21–3.17 (2H, m), 3.13–3.09 (2H, m), 1.56–1.30 (6 H, m), 1.44 (9H, s).

(t) Synthesis of Compound 5-2

With cooling in an ice bath, Compound 5-1 (4.5 g) was dissolved in a mixture solution of dry dichloromethane (50 ml) and trifluoroacetic acid (50 ml) and stirred at 4° C. for 1 hour. After removing the solvent by distillation, 50 ml of ethyl acetate containing 12% hydrochloric acid was added to the resulting residue, the solvent was distilled off again, and then the resulting residue was recrystallized from ethanol to obtain 2.6 g of the title compound in the form of white crystals.

¹H-NMR (CDCl₃) δ: 7.80–7.79 (2H, d), 7.64–7.63 (2H, d), 7.40–7.38 (2H, t), 7.32–7.29 (2H, t), 4.38–4.36 (2H, d), 3.13–3.10 (2H, t), 2.91–2.88 (2H, t), 1.67–1.64 (2H, t), 1.55–1.52 (2H, t), 1.40–1.37 (2H, t).

(u) Synthesis of Compound 5-3

Dextran having an average molecular weight of 40000 (Dextran T40, manufactured by Pharmacia) was dissolved in a mixture solution of dimethylformamide (5 ml) and 0.01% acetic acid solution (2.5 ml), and the resulting solution was added with Compound 5-2 (479 mg) and 157 mg of sodium cyanoboron hydride and stirred for 3 days at 70° C. The reaction solution was added to 75 ml of 99% ethanol and centrifuged at 3500 rpm for 10 minutes to obtain white precipitates. That was washed with 95% ethanol, acetone and ethyl ether in this order and then dried under reduced pressure to obtain 0.48 g of Compound 5-3. Progress of this reaction was confirmed by analyzing the product using a "TSK gel G4000PWXL" column (manufactured by Toso Co.) to find an Fmoc group-inherent UV absorption at 265 nm in the dextran peak detected by refractive index (RI).

(v) Synthesis of Compound 5-4

Compound 5-3 (370 mg) was dissolved in 19 ml of water, and the solution was mixed with 0.95 ml of diethylamine and stirred overnight. The reaction solution was added to 50 ml of 99% ethanol and centrifuged at 3500 rpm for 10 minutes to obtain white precipitates. That was washed with 95% ethanol, acetone and ethyl ether in this order and then dried under reduced pressure to obtain 300 mg of Compound 5-4. Progress of this reaction was confirmed by analyzing the product using a "TSK gel G4000PWXL" column (manufactured by Toso Co.) to find disappearance of an Fmoc group-inherent UV absorption at 265 nm in the dextran peak detected by refractive index (RI).

(w) Synthesis of Compound 6-1

A 0.5 g portion of pullulan having an average molecular weight of 5000 (P-5, manufactured by Showdex) was dissolved in a mixture solution of DMF (2 ml) and 0.01% acetic acid solution (5 ml), and the resulting solution was mixed with Compound 5-2 (660 mg) and 217 mg of sodium cyanoboron hydride and stirred for 3 days at 50° C. The reaction solution was added to 35 ml of 99% ethanol and centrifuged at 3500 rpm for 10 minutes to obtain white precipitates. That was washed with 95% ethanol, acetone and ethyl ether in this order and then dried under reduced pressure to obtain 0.45 g of Compound 6-1. Progress of this reaction was confirmed by analyzing the product using a "TSK gel G4000PWXL" column (manufactured by Toso Co.) to find an Fmoc group-inherent Uv absorption at 265 nm in the dextran peak detected by refractive index (RI).

(x) Synthesis of Compound 6-2

Compound 6-1 (50 mg) was dissolved in 4 ml of 0.1 N NaOH and stirred overnight. The reaction solution was added to 35 ml of 99% ethanol and centrifuged at 3500 rpm for 10 minutes to obtain white precipitates. That was washed with 95% ethanol, acetone and ethyl ether in this order and then dried under reduced pressure to obtain 36 mg of Compound 6-2. Progress of this reaction was confirmed by analyzing the product using a "TSK gel G4000PWXL" column (manufactured by Toso Co.) to find disappearance of an Fmoc group-inherent UV absorption at 265 nm in the dextran peak detected by refractive index (RI).

EXAMPLE 8

(Preparation of PEG5-rSP-IL-2):

A solution (10 ml) of rSP-IL-2 dissolved in 50 mM acetic acid buffer (pH 5.0) containing 0.25 M NaCl was applied onto a "Sephadex G-25" (SEPHADEX® G-25) column which had been equilibrated in advance with a 100 mM Tris-HCl buffer (pH 7.7) containing 10 mM calcium chloride, followed by eluting with the same buffer. The eluates were monitored by absorbance at 280 nm to obtain an eluate fraction (12 ml) of the fused protein. Compound 1-6 (413 mg) was dissolved in the above buffer (2.2 ml) and added to the eluate fraction (11 ml), and the mixture was pre-incubated at 37° C. To the reaction solution was added guinea pig liver transglutaminase (manufactured by Sigma, 6 units) dissolved in the same buffer in two portions, followed by 2 hours of incubation at 37° C.

The reaction solution was purified several times by reversed phase HPLC using a "YMC-C₈AP" column (6.0× 300 mm, manufactured by Yamamura Kagaku Co.) to remove the unreacted rSP-IL-2 fraction. With respect to the purity of the thus purified product, SDS-PAGE analysis ("Homogenious 20" gel was used) making use of "Phast System" (manufactured by Pharmacia) revealed that the PEG5 (i.e., polyethylene glycol alkylamine having an average molecular weight of 5,000)-modified form (PEG5-rSP-IL-2) gave a protein band only at the position corresponding to a molecular weight which had been increased by about 8 KDa, as compared to that of the unmodified form, assumed to be due to the bonding of one molecule of PEG5 to one molecule of the unmodified form. The yield was about 16%.

EXAMPLE 9

(Preparation of PEG10-rSP-IL-2):

A solution (5 ml) of rSP-IL-2 dissolved in 50 mM acetic acid buffer (pH 5.0) containing 0.25 M NaCl was applied onto a "Sephadex G-25" (SEPHADEX® G-25 column which had been equilibrated in advance with a 100 mM Tris-HCl buffer (pH 7.7) containing 10 mM calcium chloride, followed by eluting with the same buffer. The eluates were monitored by absorbance at 280 nm to obtain an eluate fraction (6 ml) of the fused protein. Compound 2-3 (550 mg) was dissolved in the above buffer (1.2 ml) and added to the eluate fraction (6 ml), and the mixture was pre-incubated at 37° C. To the reaction solution was added guinea pig liver transglutaminase (manufactured by Sigma, 4 units) dissolved in the same buffer in two portions, followed by 2 hours of incubation at 37° C.

The reaction solution was purified several times by reversed phase HPLC using a "YMC-$C_8$AP" column (6.0× 300 mm, manufactured by Yamamura Kagaku Co.) to remove the unreacted rSP-IL-2 fraction. With respect to the purity of the thus purified product, SDS-PAGE analysis ("Homogenious 20" gel was used) making use of "Phast System" (manufactured by Pharmacia) revealed that the PEG10 (i.e., polyethylene glycol alkylamine having an average molecular weight of 10,000)-modified form (PEG10-rSP-IL-2) gave a protein band only at the position corresponding to a molecular weight which had been increased by about 16 KDa, as compared to that of the unmodified form, assumed to be due to the bonding of one molecule of PEG10 to one molecule of the unmodified form. The yield was about 31%.

EXAMPLE 10
(Preparation of PEG5-rX1-IL-2):

Preparation of PEG5-rX1-IL-2 was carried out in accordance with the procedure of Example 8. With respect to the purity of the purified product, SDS-PAGE analysis ("Homogenious 20" gel was used) making use of "Phast System" (manufactured by Pharmacia) revealed that the PEG5-modified form (PEG5-rX1-IL-2) gave a protein band only at the position corresponding to a molecular weight which had been increased by about 8 KDa, as compared to that of the unmodified form, assumed to be due to the bonding of one molecule of PEG5 to one molecule of the unmodified form. The yield was about 15%.

EXAMPLE 11
(Preparation of PEG5-rX2-IL-2):

Preparation of PEG5-rX2-IL-2 was carried out in accordance with the procedure of Example 8. With respect to the purity of the purified product, SDS-PAGE analysis ("Homogenious 20" gel was used) making use of "Phast System" (manufactured by Pharmacia) revealed that the PEG5-modified form (PEG5-rX2-IL-2) gave a protein band only at the position corresponding to a molecular weight which had been increased by about 8 KDa, as compared to that of the unmodified form, assumed to be due to the bonding of one molecule of PEG5 to one molecule of the unmodified form.

EXAMPLE 12
(Preparation of PEG5-rX3-IL-2):

Preparation of PEG5-rX3-IL-2 was carried out in accordance with the procedure of Example 8. With respect to the purity of the purified product, SDS-PAGE analysis ("Homogenious 20" gel was used) making use of "Phast System" (manufactured by Pharmacia) revealed that the PEG5-modified form (PEG5-rX3-IL-2) gave a protein band only at the position corresponding to a molecular weight which had been increased by about 8 KDa, as compared to that of the unmodified form, assumed to be due to the bonding of one molecule of PEG5 to one molecule of the unmodified form. The yield was about 15%.

EXAMPLE 13
(Preparation of PEG5-rX4-IL-2):

Preparation of PEG5-rX4-IL-2 was carried out in accordance with the procedure of Example 8. With respect to the purity of the purified product, SDS-PAGE analysis ("Homogenious 20" gel was used) making use of "Phast System" (manufactured by Pharmacia) revealed that the PEG5-modified form (PEG5-rX4-IL-2) gave a protein band only at the position corresponding to a molecular weight which had been increased by about 8 KDa, as compared to that of the unmodified form, assumed to be due to the bonding of one molecule of PEG5 to one molecule of the unmodified form. The yield was about 15%.

EXAMPLE 14
(Preparation of PEG5-rX5-IL-2):

Preparation of PEG5-rX5-IL-2 was carried out in accordance with the procedure of Example 8. With respect to the purity of the purified product, SDS-PAGE analysis ("Homogenious 20" gel was used) making use of "Phast System" (manufactured by Pharmacia) revealed that the PEG-modified body (PEG5-rX5-IL-2) gave a protein band only at the position corresponding to a molecular weight which had been increased by about 16 KDa, as compared to that of the unmodified form, assumed to be due to the bonding of two molecules of PEG5 to one molecule of the unmodified form. The yield was about 10%.

EXAMPLE 15
(Preparation of $(Gal)_3$-rSP-IL-2)

A solution (4 ml) of rSP-IL-2 dissolved in 50 mM acetic acid buffer (pH 5.0) containing 0.25 M NaCl was applied onto a "Sephadex G-25" (SEPHADEX® G-25) column which had been equilibrated in advance with a 100 mM Tris-HCl buffer (pH 7.7) containing 10 mM calcium chloride, followed by eluting with the same Tris buffer. The eluates were monitored by absorbance at 280 nm to obtain an eluate fraction (4.8 ml) of the fused protein. Compound 3-14 (20 mg) was added to the eluate fraction (4 ml), and the mixture was pre-incubated at 37° C. To the reaction solution was added guinea pig liver transglutaminase (manufactured by Sigma, 2 units) dissolved in the Tris buffer in two portions, followed by 2 hours of incubation at 37° C.

The reaction solution was purified several times by reversed phase HPLC using a "YMC-$C_8$AP" column (6.0× 300 mm, manufactured by Yamamura Kagaku Co.) to remove the unreacted rSP-IL-2 fraction. With respect to the purity of the purified product, SDS-PAGE analysis ("Homogenious 20" gel was used) making use of "Phast System" (manufactured by Pharmacia) revealed that the $(Gal)_3$ (i.e., 3-branched type galactose alkylamine)-modified form (($Gal)_3$-rSP-IL-2) gave a protein band only at the position corresponding to a molecular weight which had been increased by about 2 KDa, as compared to that of the unmodified form, assumed to be due to the bonding of one molecule of $(Gal)_3$ to one molecule of the unmodified form. The yield was about 17%.

EXAMPLE 16
(Preparation of $(Glc)_3$-rSP-IL-2)

A solution (5 ml) of rSP-IL-2 dissolved in 50 mM acetic acid buffer (pH 5.0) containing 0.25 M NaCl was applied onto a "Sephadex G-25" (SEPHADEX® G-25) column which had been equilibrated in advance with a 100 mM Tris-HCl buffer (pH 7.7) containing 10 mM calcium chloride, followed by eluting with the same Tris buffer. The eluates were monitored by absorbance at 280 nm to obtain an eluate fraction (6 ml) of the fused protein. Compound 4-5

(90 mg) was added to the eluate fraction (4 ml), and the mixture was pre-incubated at 37° C. To the reaction solution was added guinea pig liver transglutaminase (manufactured by Sigma, 2 units) dissolved in the same buffer in two portions, followed by 2 hours of incubation at 37° C.

The reaction solution was purified several times by reversed phase HPLC using a "YMC-C$_8$AP" column (6.0× 300 mm, manufactured by Yamamura Kagaku Co.) to remove the unreacted rSP-IL-2 fraction. With respect to the purity of the thus purified product, SDS-PAGE analysis ("Homogenious 20" gel was used) making use of "Phast System" (manufactured by Pharmacia) revealed that the (Glc)$_3$ (i.e., 3-branched type glucose alkylamine)-modified form ((Glc)$_3$-rSP-IL-2) gave a protein band only at the position corresponding to a molecular weight which had been increased by about 2 KDa, as compared to that of the unmodified form, assumed to be due to the bonding of one molecule of (Glc)$_3$ to one molecule of the unmodified form. The yield was about 17%.

EXAMPLE 17
(Preparation of Dex40-rX3-IL-2):

Compound 5-4 (120 mg) was added to a solution (0.5 ml) of rX3-IL-2 dissolved in a 100 mM Tris-HCl buffer (containing 10 mM CaCl$_2$, pH 7.7), and the mixture was pre-incubated at 37° C. To the reaction solution was added guinea pig liver transglutaminase (manufactured by Sigma, 0.3 unit) dissolved in the Tris buffer, followed by 1 hour of incubation at 37° C.

The reaction solution was purified by reversed phase HPLC using a "YMC C$_8$ AP" column (manufactured by Yamamura Kagaku Co.) to remove the unreacted rX3-IL-2 fraction. With respect to the purity of the thus purified product, SDS-PAGE analysis ("Homogenious 20" gel was used) making use of "Phast System" (manufactured by Pharmacia) revealed that the Dex40 (i.e., dextran alkylamine having an average molecular weight of 40,000)-modified form (Dex40-rX3-IL-2) gave a protein band only at the position corresponding to a molecular weight which had been increased by about 100 KDa, as compared to that of the unmodified form, assumed to be due to the bonding of one molecule of Dex40 to one molecule of the unmodified form. The yield was about 10%.

EXAMPLE 18
(Preparation of Pul5-rX3-IL-2):

Compound 5-4 (60 mg) was added to a solution (0.5 ml) of rX3-IL-2 dissolved in a 100 mM Tris-HCl buffer (containing 10 mM CaCl$_2$, pH 7.7), and the mixture was pre-incubated at 37° C. To the reaction solution was added guinea pig liver transglutaminase (manufactured by Sigma, 0.3 unit) dissolved in the Tris buffer, followed by 1 hour of incubation at 37° C.

The reaction solution was purified by reversed phase HPLC using a "YMC C$_8$ AP" column (manufactured by Yamamura Kagaku Co.) to remove the unreacted rX3-IL-2 fraction. With respect to the purity of the thus purified product, SDS-PAGE analysis ("Homogenious 20" gel was used) making use of "Phast System" (manufactured by Pharmacia) revealed that the Pul5 (i.e., pullulan alkylamine having an average molecular weight of 5,000)-modified form (Pul5-rX3-IL-2) gave a protein band only at the position corresponding to a molecular weight which had been increased by about 15 KDa, as compared to that of the unmodified form, assumed to be due to the bonding of one molecule of Pul5 to one molecule of the unmodified form. The yield was about 10%.

EXAMPLE 19
(Confirmation of modified sites):

Each of freeze-dried PEG5-rSP-IL-2 (200 μg) prepared in Example 8 and freeze-dried rSP-IL-2 (200 μg) was dissolved in a 0.35 M Tris-HCl buffer (pH 8.5, 100 μl) containing 6 M guanidine hydrochloride and 35 mM EDTA, added with a DTT solution (1.2 μl, 15 mg/ml, dissolved in the same buffer) and incubated at 37° C. for 1 hour. Thereafter, iodoacetic acid solution (12 μl, 18.6 mg/ml, dissolved in the same buffer) was added to the reaction solution, and the mixture was allowed to stand for 1 hour in the dark at room temperature. After terminating the reaction by adding 2-mercaptoethanol (4 μl) and removing the reagents from the resulting solution by applying it onto a "Sephadex G-25" (SEPHADEX® G-25) column which had been equilibrated in advance with 2.5% acetic acid, the resulting protein fraction was freeze-dried to obtain reductive-alkylated PEG5-rSP-IL-2 and rSP-IL-2, respectively.

Freeze-dried powder (100 μg) of each of the thus reductive-alkylated PEG5-rSP-IL-2 and rSP-IL-2 was suspended in a 0.1 M ammonium bicarbonate buffer (pH 7.9), mixed with a "TPCK-trypsin" (manufactured by Sigma) solution (2 μl, 1 mg/ml, dissolved in the same buffer) and subjected to 4 hours of enzyme digestion at 25° C.

Figure 3A:
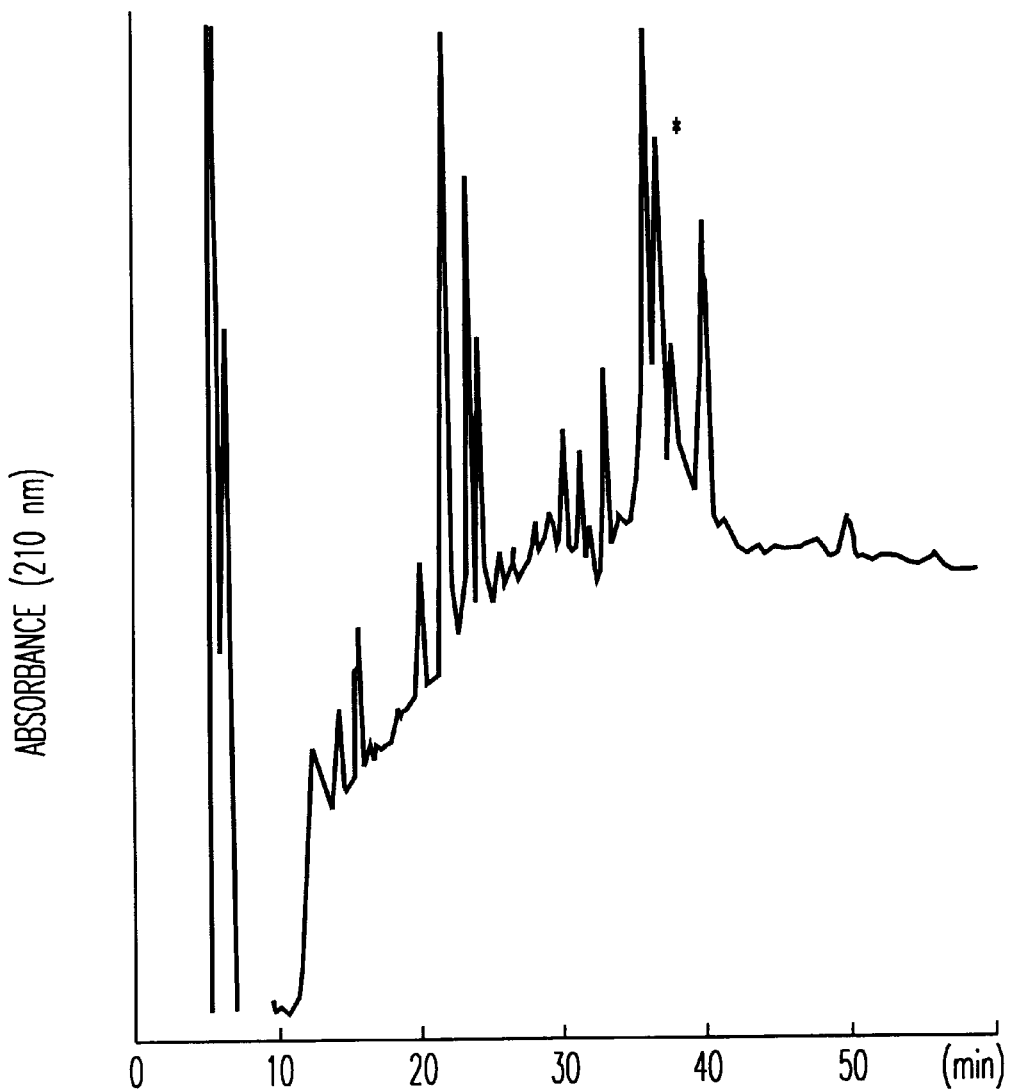
FIG. 3A is a graph showing the results in Example 19.
Figure 3B:
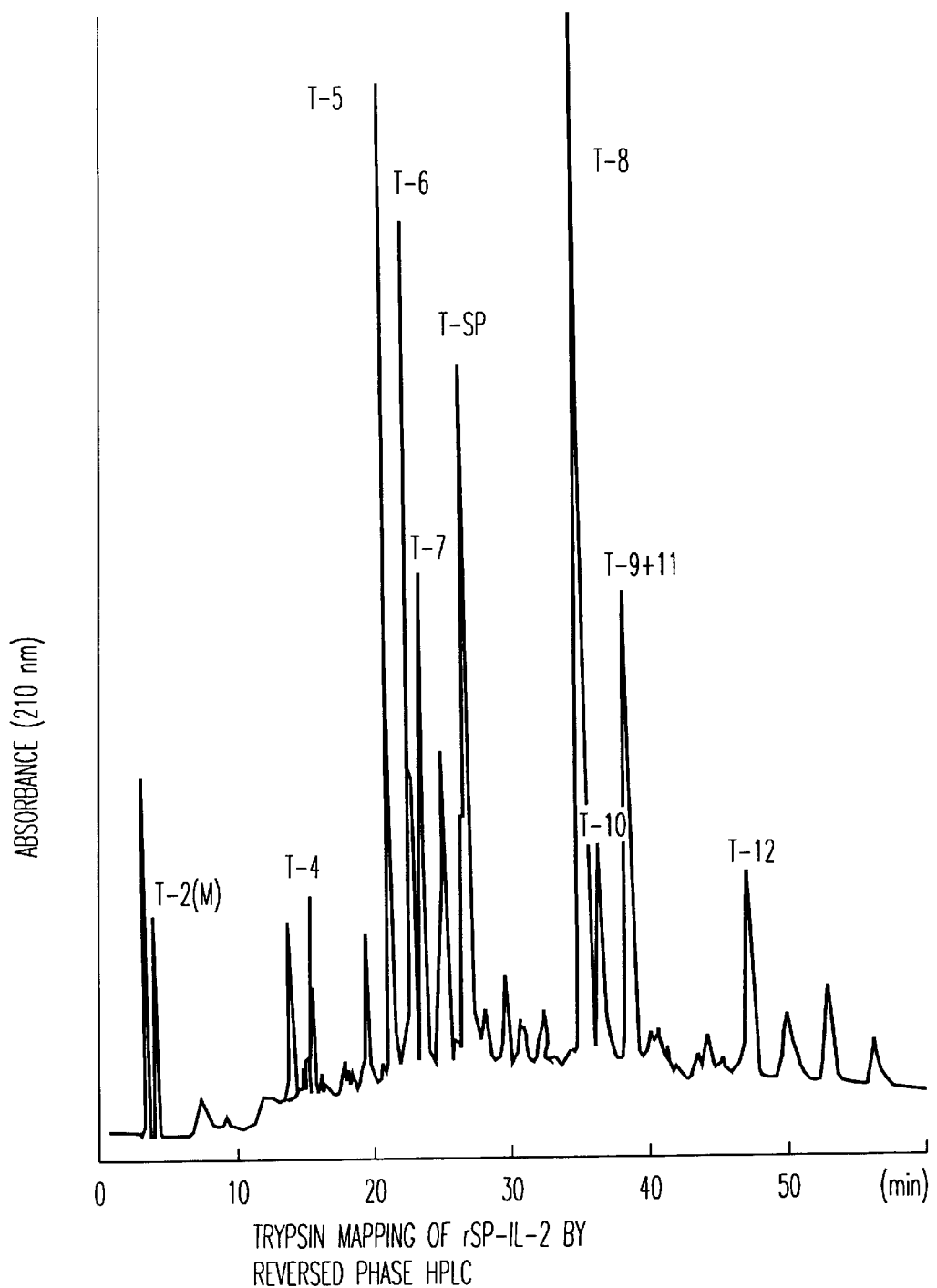
FIG. 3B is a graph showing the results in Example 19.

The reaction solution was subjected as such to reversed phase HPLC analysis using a "μBondapak C$_{18}$" (μBONDAPAK®) column (3.9×300 mm, manufactured by Waters). The results are shown in FIG. 3A and FIG. 3B. In the peptide mapping of rSP-IL-2 shown in FIG. 3B, the peak marked with T-SP corresponds to an amino acid sequence (Met-Arg-Pro-Lys-Pro-Gln-Gln-Phe-Phe-Gly-Leu-Met-Ala-Pro-Tyr-Ser-Ser-Ser-Tyr-Lys (SEQ ID NO:50)) containing an SP-originated amino acid sequence, and this peak only is absent from the peptide mapping of PEG5-rSP-IL-2 shown in FIG. 3A in which a new peak is present at a position having a different retention time. As the results, it was judged that the Gln residue in the amino acid sequence based on the SP newly added to the N-terminal side of hIL-2 was selectively modified with PEG.

EXAMPLE 20
(IL-2 activity of modified forms):

Cells of an IL-2 dependent mouse cell line "CTLL-2" (ATCC T1B 214) obtained from ATCC was cultured in a 10% FCS (fetal calf serum)-containing RPMI 1640 medium supplemented with about 50 units/ml of rat IL-2 (manufactured by Collaborative Co.). The resulting cells were washed twice with a 2% FCS-containing RPMI 1640 medium, and then suspended in a 5% FCS-containing RPMI 1640 medium to a density of 2×10$^5$ cells/ml. The thus prepared suspension was dispensed in 50 μl (104 cells) portions into the wells of a 96 well tissue culture plate and cultured after adding 50 μl of each test sample diluted with a 5% FCS-containing RPMI 1640 medium to each well. After 44 hours of the culturing, [methyl-$^3$H] thymidine (2.96 TBg/mmol) manufactured by Amersham Co. was diluted with a 5% FCS-containing RPMI 1640 medium and dispensed into wells in 37 kBq/20 μl portions, and the culturing was further continued for 4 hours. After completion of the culturing, the resulting cells were collected on a glass filter using a "PHD harvester (model 2000)" manufactured by Cambridge Technology, Inc., a scintillator ("Aquasol IL" manufactured by NEN Co.) was added to the cells, and then the radioactivity uptake was measured using a liquid scintillation counter ("TRI-CARB (model 2500TR)") manufactured by Packard Co. In this instance, purified rhIL-2 was used as the standard in the evaluation of test samples.

As the result, specific activities based on rhIL-2 were found to be 59% for rSP-IL-2, 93% for rX1-IL-2, 124% for rX2-IL-2, 94% for rX3-IL-2, 93% for rX4-IL-2, 30% for rX5-IL-2, 95% for PEG5-rSP-IL-2, 85% for PEG10-rSP-IL-2, 135% for PEG5-rX1-IL-2, 135% for PEG5-rX2-IL-2, 132% for PEG5-rX3-IL-2, 113% for PEG5-rX4-IL-2, 198% for PEG5-rX5-IL-2, and 115.4% for Pul5-rX3-IL-2, thus showing that the fused proteins and modified forms thereof retained the IL-2 activity of rhIL-2.

EXAMPLE 21
(Behavior of PEG-modified forms in the living body):

Each of 3 test samples of an un-modified rSP-IL-2, PEG5-rSP-IL-2 and PEG10-rSP-IL-2 was administered to Wistar male rats (180 to 200 g) by intravenous injection in a dose of 10 µg/kg in terms of rhIL-2 (n=3), and their blood was periodically collected to obtain blood plasma samples. Concentration of the compound in each blood plasma sample was measured by EIA (enzyme Immuno Assay "IL-2-EIA kit" manufactured by CAYMAN Co. was used).

Figure 4:
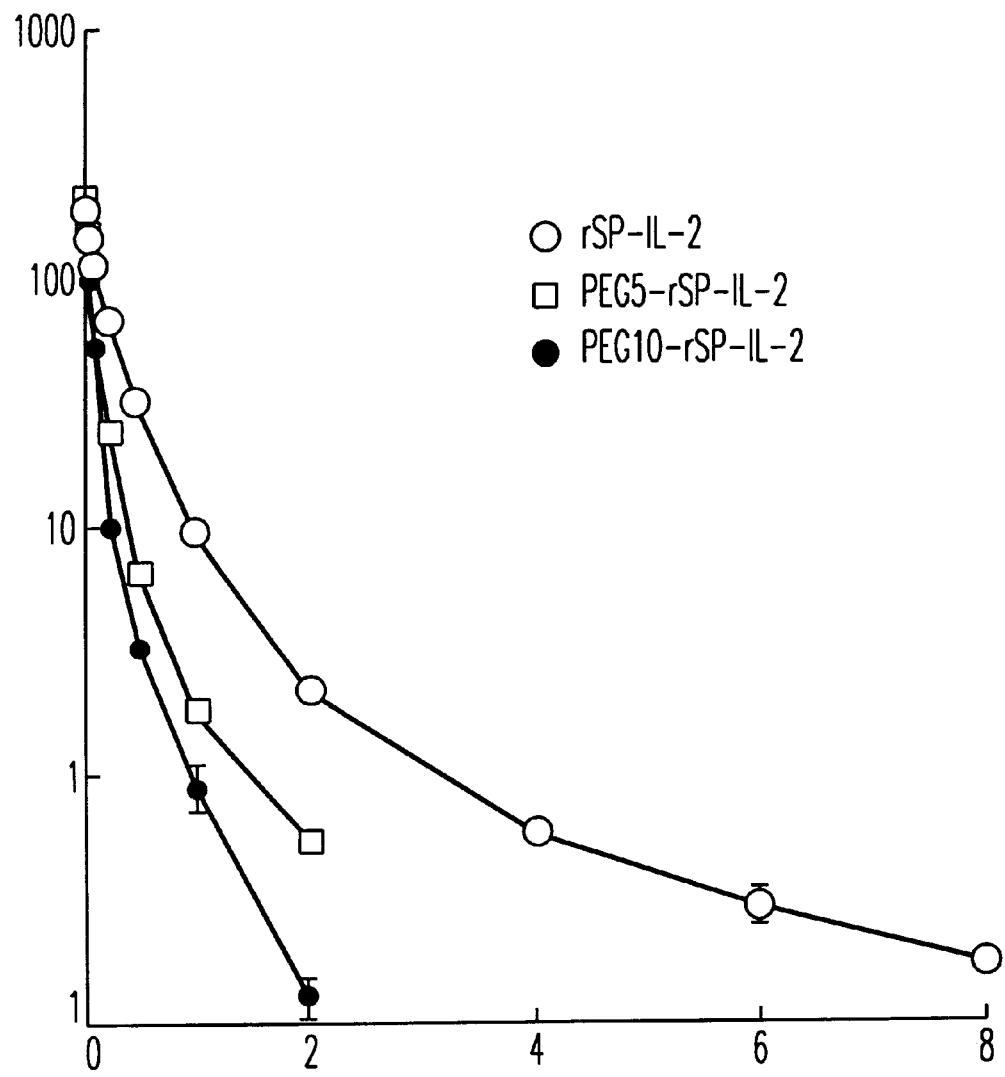
FIG. 4 is a graph showing the behavior of rSP-IL-2 derivatives in the living body (Example 21).

As the result, as shown in FIG. 4, rSP-IL-2 disappeared from the blood plasma immediately after its administration. PEG5-rSP-IL-2 modified with PEG 5000 showed slightly higher retentivity in blood than that of rSP-IL-2. On the contrary, PEG10-rSP-IL-2 modified with PEG 10000 showed markedly high retentivity in blood.

EXAMPLE 22
(Accumulativeness in tissue):

Each of rSP-IL-2, $(Gal)_3$-rSP-IL-2 and $(Glc)_3$-rSP-IL-2 was administered to Wistar male rats (7 weeks of age) by intravenous injection in a dose of 10 µg/kg (in terms of rhIL-2). Major tissues were collected after 5 minutes of the administration. Each tissue was mixed with 9 volumes of PBS, homogenized, and then subjected to 5 minutes of centrifugation at 3000 rpm, and the resulting supernatant was diluted with PBS to measure concentration of the compound in the tissue by ELISA. As the result, $(Gal)_3$-rSP-IL-2 showed a high accumulation in the liver.

INDUSTRIAL APPLICABILITY

According to the present invention, an amino group donor containing polyethylene glycol, a polysaccharide, a polyamino acid or a branched type sugar derivative can be introduced easily and selectively at the N-terminal or C-terminal of a physiologically active protein, or the peptide moiety of a fused protein of a physiologically active protein in which a peptide is linked by amide bonding to the amino acid sequence of the active protein hence facilitating the application of the physiologically active protein to pharmaceutical drugs.

What is claimed is:

1. A method of modifying a protein comprising reacting a physiologically active protein having a molecular weight of from $5 \times 10^3$ to $2 \times 10^5$ and at least one glutamine residue with an amino group donor or an alkylamine-containing polysaccharide having a molecular weight in the range of 5 kDa to 100 kDa in the presence of transglutaminase, thereby modifying said protein by forming an amido linkage between the carboxyamide group of said glutamine residue and the primary amino group of the alkylamine-containing polysaccharide or the amino group donor, wherein the amino group donor is selected from the group consisting of:

(I) $NH_2(CH_2)_nT(CH_2)_m(OCH_2CH_2)_pOR$, having a molecular weight of at least 5 kDa, (II) $NH_2(CH_2)_nT(CH_2)_m(OCH_2CH_2)_pT(CH_2)_nNH_2$, having a molecular weight of at least 5 kDa, and wherein n is an integer of 1 to 8, m is an integer of 0 to 2, p is an integer of 1 to 400, T is —O—, —C(O)O—, —OC(O)—, —NHCO—, —OCNH—, —NHCONH—, —OOCNH— or —HNCOO—, and R is a hydrogen atom, a lower alkyl group having 1 to 5 carbon atoms or a lower acyl group having 2 to 6 carbon atoms, and (III)

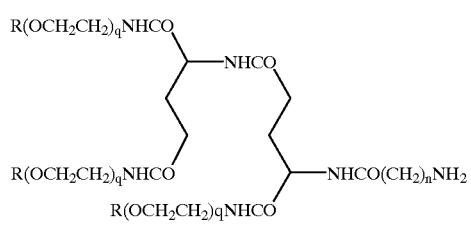

wherein n is an integer of 1 to 8, q is an integer of 2 to 6, and R is galactose, glucose or N-acetylgalactosamine, wherein said glutamine residue contained in said physiologically active protein forms an amido linkage between the γ-carboxyamide group of said glutamine residue and the primary amino group of dansylcadav-erine if 10 μM of said physiologically active protein and monodansylcadaverine in an amount of 100 equivalents per 1 equivalent of said physiologically active protein are kept at 37° C. for 60 minutes in a 100 mM Tris-HCl buffer containing 10 mM $CaCl_2$ at a pH value of 7.5, in the presence of the said transglutaminase.

2. The method of claim 1, wherein said physiologically active protein is prepared by introducing at least one peptide at the N-terminal or C-terminal of an original physiologically active protein having a molecular weight of from $5 \times 10^3$ to $2 \times 10^5$ or into the amino acid sequence of said original physiologically active protein, said peptide having 3 to 20 α-amino acids and at least one glutamine residue, the glutamine residue introduced into said original physiologically active protein forming an amido linkage between the carboxyamide group of said glutamine residue and the primary amino group of dansylcadaverine if 10 μM of the peptide-containing protein and mondansylcadaverine in an amount of 100 equivalents per 1 equivalent of said peptide-containing protein are kept at 37° C. for 60 minutes in a 100 mM Tris-buffer containing 10 mM CaCl, at a pH value of 7.5, in the presence of said transglutaminase, and said original physiologically active protein being non-reactive with dansyl cadaverine when 10 μM of said original physiologically active protein and mondansylcadaverine in an amount of 100 equivalents per 1 equivalent of said original physiologically active protein are kept at 37° C. for 60 minutes in a 100 mM Tris-buffer containing 10 mM $CaCl_2$ at a pH value of 7.5, in the presence of said transglutaminase.

3. The method of claim 2, wherein the physiologically active protein is prepared by expressing in host cells a DNA comprising a fused DNA having a DNA encoding said peptide and a DNA encoding said original physiologically active protein.

4. The method of claim 1, wherein said alkylamine-containing polysaccharide has a molecular weight in the range of 5 kDa to 40 kDa.

5. The method of claim 1, wherein the polysaccharide of said alkylamine-containing polysaccharide is selected from the group consisting of pullulan and dextran.

6. A method of making a modified protein comprising reacting a physiologically active protein having a molecular weight of from $5\times10^3$ to $2\times10^5$ and at least one glutamine residue with an amino group donor or an alkylamine-containing polysaccharide having a molecular weight in the range of 5 kDa to 100 kDa in the presence of transglutaminase, thereby modifying said protein by forming an amido linkage between the carboxyamide group of said glutamine residue and the primary amino group of the alkylamine-containing polysaccharide or the amino group donor, wherein the amino group donor is selected from the groups consisting of:

(I) $NH_2(CH_2)_nT(CH_2)_m(OCH_2CH_2)_pOR$, having a molecular weight of at least 5 kDa, (II) $NH_2(CH_2)_nT(CH_2)_m(OCH_2CH_2)_pT(CH_2)_nNH_2$, having a molecular weight of at least 5 kDa, and wherein n is an integer of 1 to 8, m is an integer of 0 to 2, p is an integer of 1 to 400, T is —O—, —C(O)O—, —OC(O)—, —NHCO—, —OCNH—, —NHCONH—, —OOCNH— or —HNCOO—, and R is a hydrogen atom, a lower alkyl group having 1 to 5 carbon atoms or a lower acyl group having 2 to 6 carbon atoms, and (III)

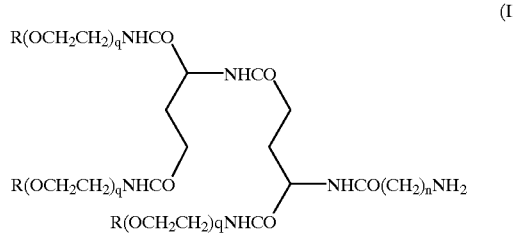

wherein n is an integer of 1 to 8, q is an integer of 2 to 6, and R is galactose, glucose or N-acetylgalactosamine, wherein said glutamine residue contained in said physiologically active protein forms an amido linkage between the γ-carboxyamide group of said glutamine residue and the primary amino group of dansylcadaverine if 10 μM of said physiologically active protein and monodansylcadaverine in an amount of 100 equivalents per 1 equivalent of said physiologically active protein are kept at 37° C. for 60 minutes in a 100 MM Tris-HCl buffer containing 10 mM $CaCl_2$ at a pH value of 7.5, in the presence of the said transglutaminase.

7. The method of claim 6, wherein said physiologically active protein is prepared by introducing at least one peptide at the N-terminal or C-terminal of an original physiologically active protein having a molecular weight of from $5\times10^3$ to $2\times10^5$ or into the amino acid sequence of said original physiologically active protein, said peptide having 3 to 20 α-amino acids and at least one glutamine residue, the glutamine residue introduced into said original physiologically active protein forming an amido linkage between the carboxyamide group of said glutamine residue and the primary amino group of dansylcadaverine when 10 μM of the peptide-containing protein and mondansylcadaverine in an amount of 100 equivalents per 1 equivalent of said peptide-containing protein are kept at 37° C. for 60 minutes in a 100 mM Tris-buffer containing 10 mM CaCl, at a pH value of 7.5, in the presence of said transglutaminase, and said original physiologically active protein being non-reactive with dansylcadaverine when 10 μM of said original physiologically active protein and mondansylcadaverine in an amount of 100 equivalents per 1 equivalent of said original physiologically active protein are kept at 37° C. for 60 minutes in a 100 mM Tris-buffer containing 10 mM $CaCl_2$ at a pH value of 7.5, in the presence of said transglutaminase.

8. The method of claim 7, wherein the physiologically active protein is prepared by expressing in host cells a DNA comprising a fused DNA having a DNA encoding said peptide and a DNA encoding said original physiologically active protein.

9. The method of claim 6, wherein said alkylamine-containing polysaccharide has a molecular weight in the range of 5 kDa to 40 kDa.

10. The method of claim 6, wherein the polysaccharide of said alkylamine-containing polysaccharide is selected from the group consisting of pullulan and dextran.

* * * * *

SEQUENCE LISTING

```
<160> NUMBER OF SEQ ID NOS: 53

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Gln Ala Gln Ser Lys Gly Asn Pro Glu Gln Thr Pro Val Leu Lys Pro
 1               5                  10                  15

Glu Glu Glu Ala
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Arg Gly Thr Cys Val Ala Ala Glu Asp Gln Arg Pro Ile Asn Tyr Cys
 1               5                  10                  15

Glu Thr Gly Leu
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3
```

Val Asp Gly Gly Cys Ser His Leu Gly Gln Ser Tyr Ala Asp Arg Asp
1               5                   10                  15

Val Trp Lys Pro
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Ser Ser Gly Thr Gly Ser Thr Gly Asn Gln Asn Pro Gly Ser Pro Arg
1               5                   10                  15

Pro Gly Ser Thr
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Glu Ser Ser Val Ser Gly Ser Thr Gly Gln Trp His Ser Glu Ser Gly
1               5                   10                  15

Ser Phe Arg Pro
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Asn Arg Leu Thr Ile Gly Glu Gly Gln Gln His His Leu Gly Gly Ala
1               5                   10                  15

Lys Gln Ala Gly
            20

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Glu Ala Gln Gln Ile Val Gln Pro Gln Ser Pro Leu Thr
1               5                   10

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: synthetic peptide

<400> SEQUENCE: 8

Lys Pro Lys Met Cys Pro Gln Leu Gln Gln Tyr Glu Met His Gly Pro
 1               5                  10                  15

Glu Gly Leu Arg
            20

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Asn Gln Glu Gln
 1

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 10

His Ser Gln Gly Thr Phe Thr Ser Asp Tyr Ser Lys Tyr
 1               5                  10

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Ser Lys Tyr Leu Asp Ser Arg Arg Ala Gln Asp Phe Val Gln Trp Leu
 1               5                  10                  15

Met Asn Thr

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 12

Pro Pro Gln Ser Val Leu Ser Leu Ser Gln Ser Lys Val Leu Pro Val
 1               5                  10                  15

Pro Glu Lys Ala
            20

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

```
<400> SEQUENCE: 13

Ala Leu Trp Gln Phe Arg Ser Met Ile Lys Cys Ala Ile Pro
 1               5                  10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Ala Lys Lys Lys Arg Ser Arg Phe Asp Gln Asp Val Leu Asn
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15

Leu Ile Ser Trp Ile Lys Arg Lys Arg Gln Gln
 1               5                  10

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 16

Gln Ala Trp Phe Ile Glu Asn Glu Glu Gln Glu Tyr Val Gln Thr Val
 1               5                  10                  15

Lys Ser Ser Lys
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 17

Pro Ser Ile Val Gly Arg Pro Arg His Gln Gly Val Met Val Gly Met
 1               5                  10                  15

Gly Gln Lys Asp
            20

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 18
```

```
Ala Ser Asn His Glu Thr Gln Ala Gly Lys Pro Gln Pro Leu Asn Pro
 1               5                  10                  15
Lys

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 19

Ala Glu Gln His Ser Thr Pro Glu Gln Ala Ala Ala Gly
 1               5                  10

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 20

Glu Thr Gln Thr Val Gln Gln Glu Leu Glu Ser Leu Pro Thr Thr Lys
 1               5                  10                  15

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 21

Glu Ala Gln Leu Glu Leu Pro Glu Gln Gln Val Gly Gln Pro Lys His
 1               5                  10                  15
Leu Glu Gln Gln
            20

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 22

Ser Ser Gly Gly Gly Gly Phe Ser Gly Gln Ala Val Gln Cys Gln Ser
 1               5                  10                  15
Tyr Gly Gly Val
            20

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 23

Gly Ser Gly Ser Gly Tyr Val Ser Ser Gln Gln Val Thr Gln Thr Ser
```

-continued

```
                1               5              10              15
Cys Ala Pro Gln
            20
```

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 24

```
Gly Tyr Val Ser Ser Gln Gln Val Thr Gln Thr Ser Cys Ala Pro Gln
 1               5                  10                  15

Pro Ser Tyr Gly
            20
```

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 25

```
Lys Tyr Gly Val Thr Asp Lys Ile Ser Gln Val Ser Thr Gly Gly Gly
 1               5                  10                  15

Ala Ser Leu Glu
            20
```

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 26

```
Gly Gly Phe Met Tyr Ser Asp Lys Ser Gln Thr Pro Leu Val
 1               5                  10
```

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 27

```
Met Arg Pro Lys Pro Gln Gln Phe Phe Gly Leu Met
 1               5                  10
```

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 28

```
Arg Phe Ser Asn Cys Gly Leu Gly Ser Gln Ala Gly Ile Arg Asp Met
```

```
1               5              10             15
```

Arg Gly Gly Phe
         20

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 29

Met Lys Pro Gln Gln Phe Phe Gly Leu
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 30

Ala Pro Tyr Ser Ser
 1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 31

Lys Pro Gln Gln Phe
 1               5

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 32
cgttaaatgc gtccaaaacc gcagcagttc ttcggtct                            38

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 33
catgagaccg aagaactgct gcggttttgg acgcatttaa                          40

<210> SEQ ID NO 34
<211> LENGTH: 11
<212> TYPE: PRT
<213> ORGANISM: Artificial Sequence
<220> FEATURE:

```
<223> OTHER INFORMATION: Description of Artificial Sequence: synthetic
      peptide

<400> SEQUENCE: 34

Met Arg Pro Lys Pro Gln Gln Phe Phe Gly Leu
 1               5                  10

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 35
cgttaaatgc gtccaaaacc tcagcagtt                                    29

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 36
catgaactgc tgaggttttg gacgcattta a                                 31

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 37

Met Arg Pro Lys Pro Gln Gln Phe Met
 1               5

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 38
cgttaaatgc caaaacctca gcagtt                                       26

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 39
catgaactgc tgaggttttg gcatttaa                                     28

<210> SEQ ID NO 40
<211> LENGTH: 8
<212> TYPE: PRT
<213> ORGANISM: Artificial Sequence
```

<220> FEATURE:
<223> OTHER INFORMATION: Description of Artificial Sequence: synthetic
      peptide

<400> SEQUENCE: 40

Met Pro Lys Pro Gln Gln Phe Met
 1               5

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 41
cgttaaatga aacctcagca gtt                                              23

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 42
catgaactgc tgaggtttca tttaa                                            25

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 43

Met Lys Pro Gln Gln Phe Met
 1               5

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 44
cgttaaatgg ctctgtgtgg cagtttcg                                         28

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 45
catgcgaaac tgccacagag ccatttaa                                         28

<210> SEQ ID NO 46
<211> LENGTH: 8
<212> TYPE: PRT

```
<213> ORGANISM: Artificial Sequence
<220> FEATURE:
<223> OTHER INFORMATION: Description of Artificial Sequence: synthetic
      peptide

<400> SEQUENCE: 46

Met Ala Leu Trp Gln Phe Arg Met
 1               5

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 47
cgttaaatgg ctcagcagat cgt                                           23

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 48
catgacgatc tgctgagcca tttaa                                         25

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 49

Met Ala Gln Gln Ile Val Met
 1               5

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 50

Met Arg Pro Lys Pro Gln Gln Phe Phe Gly Leu Met Ala Pro Tyr Ser
 1               5                  10                  15

Ser Ser Tyr Lys
            20

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 51
cgttaaatgc gtccaaaacc gcagcagttc ttcggtctca tg                      42
```

-continued

```
<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: synthetic
      DNA fragment

<400> SEQUENCE: 52
catgagaccg aagaactgct gcggttttgg acgcatttaa                              40

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 53

Met Arg Pro Lys Pro Gln Gln Phe Phe Gly Leu Met
 1               5                  10
```